United States Patent
Corley

(10) Patent No.: US 12,102,145 B2
(45) Date of Patent: Oct. 1, 2024

(54) MATERIAL AND APPAREL THAT POSITIVELY AFFECT THE HEALTH AND WELLBEING OF A MAMMAL

(71) Applicant: Incrediwear Holdings, Inc., Chico, CA (US)

(72) Inventor: Jackson Corley, Chico, CA (US)

(73) Assignee: Incrediwear Holdings, Inc., Chico, CA (US)

( * ) Notice: Subject to any disclaimer, the term of this patent is extended or adjusted under 35 U.S.C. 154(b) by 0 days.

(21) Appl. No.: 18/451,796

(22) Filed: Aug. 17, 2023

(65) Prior Publication Data
US 2024/0197003 A1  Jun. 20, 2024

Related U.S. Application Data

(60) Provisional application No. 63/387,486, filed on Dec. 14, 2022, provisional application No. 63/387,453, filed on Dec. 14, 2022.

(51) Int. Cl.
A41D 13/05 (2006.01)
A61N 1/04 (2006.01)
A61N 1/20 (2006.01)

(52) U.S. Cl.
CPC .......... *A41D 13/05* (2013.01); *A41D 2400/32* (2013.01)

(58) Field of Classification Search
CPC .................................................... A61N 1/0484
See application file for complete search history.

(56) References Cited

U.S. PATENT DOCUMENTS

| 5,607,453 | A | 3/1997 | Ishiguro et al. |
| 5,848,985 | A | 12/1998 | Muroki |
| 5,944,685 | A | 8/1999 | Muroki |
| 10,905,894 | B2 | 2/2021 | Karpf |
| 11,000,695 | B2 | 5/2021 | Liang |
| 11,617,527 | B2 | 4/2023 | Majava et al. |
| 2016/0166830 | A1 | 6/2016 | Avent et al. |

(Continued)

FOREIGN PATENT DOCUMENTS

| CN | 203187840 U | 9/2013 |
| CN | 214207216 U | 9/2021 |

(Continued)

OTHER PUBLICATIONS

Marino, Katherine et al., "Effect of Germanium-Embedded Knee Sleeve on Osteoarthritis of the Knee", The Orthopedic Journal of Sports Medicine, Oct. 25, 2019, 7 pages.
U.S. Appl. No. 18/451,788, filed Aug. 17, 2023 titled Material and Apparel That Positively Affect the Health and Wellbeing of a Mammal, pp. 1-87.
U.S. Appl. No. 18/451,790, filed Aug. 17, 2023 titled Material and Apparel That Positively Affect the Health and Wellbeing of a Mammal, pp. 1-87.

(Continued)

*Primary Examiner* — Brian T Gedeon
(74) *Attorney, Agent, or Firm* — Stephen A. Gratton

(57) ABSTRACT

A material and apparel that positively affect the health and well-being of a mammal include fibers that are formed with a semiconductor. Upon contact of the material or apparel with a region of the mammal's body, a positive effect occurs that relates to the health and wellbeing of that mammal. The material includes a region that includes an expanse. The expanse is formed with a semiconductor and constructed for contact with the skin of the mammal. The apparel has a body that includes a region that has a wearable form made of a semiconductor, and is constructed for making contact with a human body when the human wears the apparel.

12 Claims, 22 Drawing Sheets

(56) References Cited

U.S. PATENT DOCUMENTS

2019/0281908 A1    9/2019  Park
2021/0330100 A1*  10/2021  Ureten .................... A61N 1/16
2022/0134124 A1    5/2022  Liang et al.

FOREIGN PATENT DOCUMENTS

| JP | 10179764 A    | 7/1998 |
| JP | 2000160402 A  | 6/2000 |
| JP | 2002065864 A  | 3/2002 |
| KR | 101995170 B1  | 7/2019 |
| KR | 20190105291 A | 9/2019 |
| KR | 10-2424727 B1 | 7/2022 |
| WO | 2016093632 A1 | 6/2016 |

OTHER PUBLICATIONS

U.S. Appl. No. 18/451,801, filed Aug. 17, 2023 titled Material and Apparel That Positively Affect the Health and Wellbeing of a Mammal, pp. 1-87.
U.S. Appl. No. 18/451,793, filed Aug. 17, 2023 titled Material and Apparel That Positively Affect the Health and Wellbeing of a Mammal, pp. 1-87.
U.S. Appl. No. 18/451,795, filed Aug. 17, 2023 titled Material and Apparel That Positively Affect the Health and Wellbeing of a Mammal, pp. 1-87.
U.S. Appl. No. 18/451,800, filed Aug. 17, 2023 titled Material and Apparel That Positively Affect the Health and Wellbeing of a Mammal, pp. 1-87.
Translation for KR 10-2424727 B1 (Year 2022), pp. 1-12.

* cited by examiner

| Material Composition (%) | Cotton (Germanium Infused) | Cotton (Germanium Carbonized Charcoal infused) | Polyester (Carbonized Charcoal Infused) | Polyester | Polyester (Germanium Carbonized Charcoal infused) | Polyester (Germanium Infused) | Nylon (Germanium Infused) | Nylon | Spandex | Rubber | Viscose |
|---|---|---|---|---|---|---|---|---|---|---|---|
| Product / Trade Name | | | | | | | | | | | |
| Arm Sleeve | 27% | | 63%-74% | | | | | 18%-27% | 8%-10% | | |
| Elbow Sleeve | | | 26%-34% | | | | 32%-41% | | 6%-7% | | |
| Wrist Sleeve | 37% | | 30% | | | | 30% | | 3% | | |
| Shoulder Brace | | | | | 53% | | | 30% | | 11% | |
| Circulation Gloves | | | 20% | | | | | | 6% | 80% | 80% |
| Circulation Gloves | | | 20% | | | | | | | | 80% |
| Knee Sleeve | 21% | | 49% | | | | 25% | | 5% | | |
| Ankle Sleeve | 34% | | 28% | | | | 33% | | 5% | | |
| Calf Sleeve | | | 63%-74% | | | | | 18%-27% | 8%-10% | | |
| Recovery Leg Sleeve | | | 66% | | | | | 24% | 10% | | |
| Walking Boot | 27% | | 46% | | | | 22% | | 5% | | |
| Undersleeve | | | | | | 45% | | 42% | 13% | | |
| Hip Brace | | | | | 54% | | | 23% | 2% | 21% | |
| Body Sleeve | | | | | | 45% | | 42% | 13% | | |
| Back Brace | | 20% (inside) | | 30%-61% | | | | 10%-30% | 2% | | |
| Bandage Wrap | | | | 70% | | | | 15% | 15% | | |

Figure 1

| Product | Components and concentration Ranges | Size of the Product |
|---|---|---|
| Active Low Cut Socks | 57% Bamboo Charcoal Fiber; 28% Cotton; 15% Flexible Fiber | Small (S), Medium (M), Large (L), Extra-large (XL) |
| Trek Crew | 22% Bamboo Charcoal Fiber;48% Cotton; 30% Flexible Fiber | S, M, L, XL |
| Trek Crew | 78% Germanium/Bamboo Charcoal Fiber; 22% Flexible Fiber | S, M, L, XL |
| Trek Crew | 24% Bamboo Charcoal Fiber; 54% Cotton; 7% Nylon; 8% Rubber; 7% Spandex | S, M, L, XL |
| Active Quarter Socks | 50% Bamboo Charcoal Fiber; 33% Cotton; 17% Flexible Fiber | S, M, L |
| Run Socks-Low Cut | 55% Bamboo Charcoal Fiber; 36% Flexible Fiber; 9% Lycra | S, M, L |
| Sport Socks- Thin- No Show/ Quarter/ Thin Crew | 52% Carbonized Charcoal; 28% Lycra; 8% Nylon; 7% Rubber | S, M, L |
| CIRCULATION SOCKS - Ankle | 36% Cotton (Germanium Infused); 34%Polyester(Carbon Infused); 26%Nylon(Germanium Infused); 4%Spandex | S, M, L |
| CIRCULATION SOCKS - Crew | 38% Cotton (Germanium Infused), 33%Polyester(Carbon Infused); 25%Nylon(Germanium Infused); 4%Spandex | S, M, L |
| Sports Socks Low Cut | 70% Polyester(Carbonized Charcoal Infused); 15% Cotton; 10% Nylon; 5% Spandex | S, M, L, XL |
| Sports Socks Quarter | 71% Polyester (Carbonized Charcoal Infused); 14% Cotton; 10% Nylon; 5% Spandex | S, M, L, XL |
| Sports Socks CREW | 75% Polyester(Carbonized Charcoal Infused); 10% Cotton; 9% Nylon; 6 % Spandex | S, M, L, XL |
| Boot Sleeve | 27% Cotton; 22% Nylon; 46% Polyester; 5% Lycra Spandex (CW 40(Germanium, Carbonized Charcoal Blend) | S, M, L, XL |
| Knee Brace | 49% Polyester(Carbon Infused); 25% Nylon(Germanium Infused); 21% Cotton(Germanium Infused); 5% Lycra Spandex | S, M, L, XXL, XXXL |
| Ankle Brace | 34% Cotton(Germanium Infused); 33% Nylon(Germanium Infused); 28% Polyester(Carbon Infused);5% Lycra Spandex | S, M, L, XL |
| Calf Sleeve | 63% Polyester(Carbon Infused);27% Nylon; 10% Lycra Spandex | S, M, L |
| Arm Sleeve | 63% Polyester(Carbon Infused);27% Nylon; 10% Lycra Spandex | S, M, L |
| Back Brace | Inside: 40% Polyester ; 21% Nylon ; 19% Cotton (Germanium/carbon Infused) ,20% Spandex , Outside: 43% Nylon; 37% Rayon; S, M, L, XL, XXL, XXXL |

Figure 22

MATERIAL AND APPAREL THAT POSITIVELY AFFECT THE HEALTH AND WELLBEING OF A MAMMAL

CROSS-REFERENCE TO RELATED APPLICATIONS

This application claims priority to U.S. Provisional Patent Application Ser. No. 63/387,453, filed Dec. 14, 2022 and U.S. Provisional Patent Application Ser. No. 63/387,486, filed Dec. 14, 2022, both entitled MATERIAL AND APPAREL THAT POSITIVELY AFFECT THE HEALTH AND WELLBEING OF A MAMMAL, the disclosures of which are incorporated herein by reference.

FIELD OF THE INVENTION

Embodiments of the inventions relate to a material and apparel that positively affect the health and wellbeing of a mammal.

BACKGROUND OF THE INVENTION

Symptoms like pain and swelling are associated with various diseases such as arthritis, inflammation, edema, infection, and various injuries. Also, there are conditions that cause pain, such as sprains, muscle strains and tears, and cramps, each of which negatively affect a mammal's body, including a human's body. Patients with pain experience decreased mobility and function, muscle weakness, and deterioration in their ability to accomplish daily activities.

Conventional systems and methods are available for treating existing diseases and conditions that involve taking medications, or performing diagnostic and therapeutic surgeries. However, those systems and methods involve ingesting substances or invasive activity, and often do not provide long-lasting solutions.

Alternative treatments for these diseases are desirable to provide long-lasting solutions that do not involve ingesting substances or invasive activity, effectively to relieve pain and improve function and, to delay surgery, and to delay or eliminate the need for taking medications.

SUMMARY OF THE INVENTION

The inventions (also referred to collectively as "the present invention") concern a material and apparel that positively affect the health and wellbeing of a mammal. The present invention affects a mammal upon contact with the mammal's outer body, such as their skin, fur or hide. One positive affect may be characterized as a therapeutic one.

In accordance with an embodiment of the present invention, the material and the apparel include at least one fiber formed with a semiconductor, such as germanium. The semiconductor is selected from a group of semiconductors that includes germanium. To utilize the germanium in accordance with the invention, the germanium is ground into a powder of nanoparticles that are doped into fibers of cotton, nylon or polyester.

In one general aspect, the inventions relate to the material for contacting the mammal with the body that includes a region that is experiencing swelling. An expanse of the material is formed with a semiconductor and constructed for contact with that region, and the contact causes a decrease in the swelling.

In accordance with another embodiment of the present invention, it is formed as apparel for the human whose body includes a region that is experiencing swelling. The apparel is formed with a semiconductor and constructed for contact with an outer region of a mammal when the mammal wears the apparel. Upon contact with that, the apparel causes a decrease in the swelling. As used herein, apparel may be a shirt, pants, dress, underwear, socks, clothing, or a sleeve.

In accordance with another embodiment of the present invention, the material for contacting the mammal with the body includes a region that has a wound that requires a first time to heal fully. An expanse is formed with a semiconductor and constructed for contact with that region, and the contact causes the wound to heal in a second time that is less than the first time.

In accordance with another embodiment of the present invention, it is formed as apparel for a human whose body includes a region that has a wound that requires a first time to heal fully. The apparel is formed with a semiconductor and constructed for contact with an outer region of a mammal when the mammal wears the apparel. Upon contact with that, the apparel causes the wound to heal in a second time that is less than the first time.

In accordance with an embodiment of the present invention, the material for contacting the mammal with the body includes a region that has a wound that requires a first time for the body to recover fully. An expanse is formed with a semiconductor and constructed for contact with that region, and the contact causes the body to recover in a second time that is less than the first time.

In accordance with another embodiment of the present invention, it is formed as apparel for a human whose body that includes a region that has a wound that requires a first time for the body to recover fully. The apparel is formed with a semiconductor and constructed for contact with an outer region of a mammal when the mammal wears the apparel. Upon contact with that, the apparel causes the body to recover in a second time that is less than the first time.

In accordance with another embodiment of the present invention, the material for contacting the mammal with the body includes mobile cells that move within the body and exhibit cellular movement at a first rate. An expanse is formed with a semiconductor and constructed for contact with that region, and the contact causes the cellular movement to occur at a second rate that is greater than the first rate.

In accordance with another embodiment of the present invention, it is formed as apparel for a human whose body that includes mobile cells that move within the body and exhibit cellular movement at a first rate. The apparel is formed with a semiconductor and constructed for contact with an outer region of a mammal when the mammal wears the apparel. Upon contact with that, the apparel causes the cellular movement to occur at a second rate that is greater than the first rate.

In accordance with another embodiment of the present invention, the material for contacting the mammal with the body is capable of receiving external optical waves. An expanse is formed with a semiconductor and constructed for contact with that region, and the contact causes an external mid-IR optical wave to be received by the body.

In accordance with another embodiment of the present invention, it is formed as apparel for a human whose body is capable of receiving an optical wave. The apparel is formed with a semiconductor and constructed for contact with an outer region of a mammal when the mammal wears the apparel. Upon contact with that, the apparel causes an external mid-IR optical wave to be received by the body.

In accordance with another embodiment of the present invention, the material for contacting the mammal with the skin-covered, tissue-containing body is capable of experiencing temperature changes in spite of being warm-blooded. An expanse is formed with a semiconductor and constructed for contact with that region, and the contact promotes thermoregulation of the body by cooling the body when it exceeds a first temperature and heating it when it falls below a second temperature.

In accordance with another embodiment of the present invention, it is formed as apparel for a human whose skin-covered, tissue-containing body that is capable of experiencing temperature changes in spite of being warm-blooded. The apparel is formed with a semiconductor and constructed for contact with an outer region of a mammal when the mammal wears the apparel. Upon contact with that, the apparel promotes thermoregulation of the body.

In accordance with another embodiment of the present invention, the material for contacting the mammal with a body that has arthritis, experiences pain, and has decreased physical capabilities due to the arthritis. An expanse is formed with a semiconductor and constructed for contact with that region, and the contact treats the arthritis by reducing pain and improving physical capabilities chosen from the groups consisting of grip and range of motion.

In accordance with another embodiment of the present invention, it is formed as apparel for a human whose body has arthritis, experiences pain, and has decreased physical capabilities due to the arthritis. The apparel is formed with a semiconductor and constructed for contact with an outer region of a mammal when the mammal wears the apparel. Upon contact with that, the apparel treats the arthritis by reducing pain and improving physical capabilities chosen from the groups consisting of grip and range of motion.

In accordance with another embodiment of the present invention, the material for contacting the human with the body is capable of playing sports and getting sports injuries. An expanse is formed with a semiconductor and constructed for contact with that region, and the contact tends to prevent sports injuries.

In accordance with another embodiment of the present invention, it is formed as apparel for a human with a body that is capable of playing sports and getting sports injuries. The apparel is formed with a semiconductor and constructed for contact with an outer region of a mammal when the mammal wears the apparel. Upon contact with that, the apparel tends to prevent sports injuries.

In accordance with another embodiment of the present invention, the material for contacting the human with the body has a neurological system, tissue, and blood that includes nutrient-containing hemoglobin, and the tissue is capable of being oxygenated and receiving nutrients by the hemoglobin in the blood that flows through the tissue. An expanse is formed with a semiconductor and constructed for contact with that region, and the contact tends to decrease neuropathy in the body by increasing the flow of hemoglobin-containing blood through the tissue.

In accordance with another embodiment of the present invention, it is formed as apparel for a human with a body that has a neurological system, tissue, and blood that includes nutrient-containing hemoglobin, and the tissue is capable of being oxygenated and receiving nutrients by the hemoglobin in the blood that flows through the tissue. The apparel is formed with a semiconductor and constructed for contact with an outer region of a mammal when the mammal wears the apparel. Upon contact with that, the apparel tends to decrease neuropathy in the body by increasing the flow of hemoglobin-containing blood through the tissue.

In accordance with another embodiment of the present invention, the material for contacting the human with a body has cognitive function and is capable of experiencing a concussion that causes headaches. An expanse is formed with a semiconductor and constructed for contact with that region, and the contact tends to promote healing after a concussion. That contact promotes healing after the concussion by restoring cognitive function and, as a result, tends to reduce headaches.

In accordance with another embodiment of the present invention, it is formed as apparel for a human with a body that has cognitive function and is capable of experiencing a concussion that causes headaches. The apparel is formed with a semiconductor and constructed for contact with an outer region of a mammal when the mammal wears the apparel. Upon contact with that, the apparel tends to promote healing after a concussion by restoring cognitive function and, as a result, tends to reduce headaches.

In accordance with another embodiment of the present invention, the material for contacting the human with a body is capable of experiencing headaches. An expanse is formed with a semiconductor and constructed for contact with that region, and the contact tends to reduce headaches.

In accordance with another embodiment of the present invention, it is formed as apparel for a human with a body that is capable of experiencing headaches. The apparel is formed with a semiconductor and constructed for contact with an outer region of a mammal when the mammal wears the apparel. Upon contact with that region, the apparel tends to reduce headaches.

In accordance with another embodiment of the present invention, the material is for contacting the human with a body that contains positive ions. An expanse is formed with a semiconductor and constructed for contact with that region. That contact releases negative ions that enter the body and pair with the positive ions, causing an exothermic reaction that cools the body adjacent the region where the pairing of negative ions and positive ions occurs.

In accordance with another embodiment of the present invention, it is formed as apparel for a human with a body that contains positive ions. The apparel is formed with a semiconductor and constructed for contact with an outer region of a mammal when the mammal wears the apparel. Upon contact with that, the apparel releases negative ions that enter the body and pair with the positive ions, causing an exothermic reaction that cools the body adjacent the region where the pairing of negative ions and positive ions occurs.

In accordance with another embodiment of the present invention, the material is for contacting the human with the body that is capable of experiencing muscle load. An expanse is formed with a semiconductor and constructed for contact with that region, and the contact tends to decrease muscle load in the body.

In accordance with another embodiment of the present invention, it is formed as apparel for a human with a body that is capable of experiencing muscle load. The apparel is formed with a semiconductor and constructed for contact with an outer region of a mammal when the mammal wears the apparel. Upon contact with that, the apparel tends to decrease muscle load in the body.

In accordance with another embodiment of the present invention, the material is for contacting the human with the body that includes tissue, blood vessels and cells, and in which there is interstitial fluid pressure that relates to interstitial fluid that is extracellular and outside of blood vessels. An expanse is formed with a semiconductor and constructed for contact with that region, and the contact tends to increase the interstitial fluid pressure in the body.

In accordance with another embodiment of the present invention, it is formed as apparel for a human with a body that includes tissue, blood vessels and cells, and in which there is interstitial fluid pressure that relates to interstitial fluid that is extracellular and outside of blood vessels. The apparel is formed with a semiconductor and constructed for contact with an outer region of a mammal when the mammal wears the apparel. Upon contact with that, the apparel tends to increase the interstitial fluid pressure in the body.

In accordance with another embodiment of the present invention, the material is for contacting the human with the body that includes a brain, sensory receptors, muscles, and a proprioception system. An expanse is formed with a semiconductor and constructed for contact with that region, and the contact tends to balance the muscles in the body by creating a proprioceptive response within the proprioception system.

In accordance with another embodiment of the present invention, it is for apparel for a human with a body that includes a brain, sensory receptors, muscles, and a proprioception system. The apparel is formed with a semiconductor and constructed for contact with an outer region of a mammal when the mammal wears the apparel. Upon contact with that, the apparel tends to balance the muscles in the body by creating a proprioceptive response within the proprioception system.

In accordance with another embodiment of the present invention, the expanse is formed as a geometric shape so that it can be worn by a mammal, and preferably, a human.

The above summaries, and other embodiments and advantages of the present disclosure (also referred to as disclosure) will become readily apparent to PHOSITAs (people having ordinary skill in the art) from the following detailed description of the embodiments, and with reference to the attached figures. The disclosure is not limited to any particular one of the several disclosed embodiments.

BRIEF DESCRIPTION OF THE DRAWINGS

To understand the inventions in detail, a more particular description of the inventions, briefly summarized above, is also provided below, by reference to embodiments, some of which are illustrated in the appended drawings. The appended drawings illustrate typical embodiments of the inventions and therefore do not limit their scope, for the inventions may have other, equally effective embodiments.

FIG. 1 illustrates a Table 1 which shows different compositions used for preparing apparel 101 in accordance with an embodiment of the invention;

FIG. 22 illustrates a Table 2 that shows different components and concentrations ranges used for preparing apparel 101, in accordance with another exemplary embodiment of the invention.

LIST OF ITEMS DESCRIBED BELOW

Figure 2:
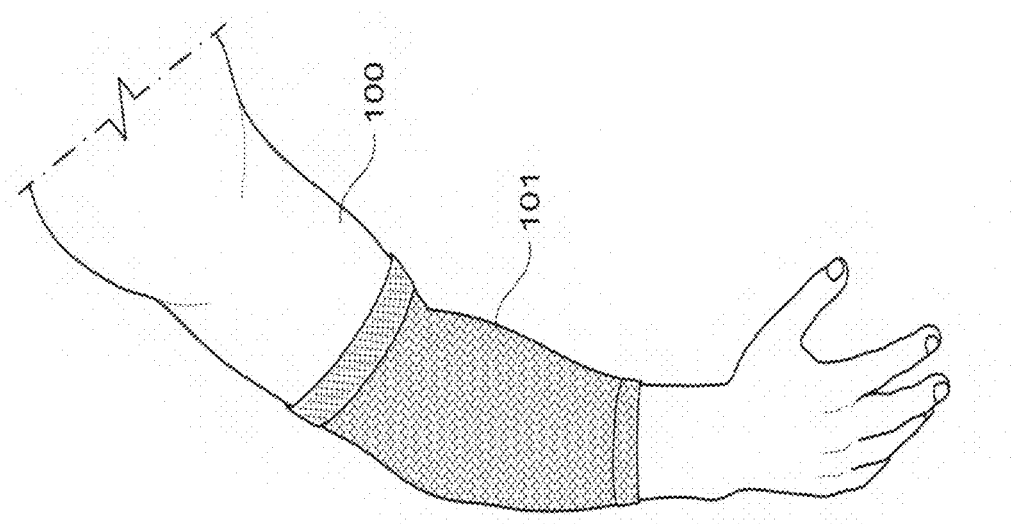
FIG. 2 shows a human arm 100 covered by the material/apparel 101 worn by a wearer which upon contact 102 with the region of the wearer causes a decrease in the swelling or reduces pain or helps in blood circulation, in accordance with an embodiment of the invention.

Human arm 100
Material/Apparel 101
Contact 102
Skin 103
External mid-IR optical wave 104
Right leg sleeve 105
Swollen arm 106
cellular movement at a first speed/rate 107 cellular movement at a second speed/rate 108
Human upper body part 109
Human lower body part 110
Human palm 111
Fiber thread 112

DETAILED DESCRIPTION

Embodiments of the present invention are described more fully below with reference to the accompanying drawings, in which reference numerals represent like elements throughout the several figures, and in which example embodiments are shown. Embodiments of the claims may, however, be embodied in many different forms and should not be construed as limited to the embodiments set forth in the following description. The example embodiments are non-limiting, and show some of many possible examples.

In the following description, forming a first described feature adjacent a second feature may include embodiments in which the first and second features are formed in direct contact, and others where additional features may be formed interposing the first and second features, so the first and second features may not be in direct contact.

Some embodiments of the invention, illustrating features, will now be discussed in detail. The words "comprising," "having," "containing," and "including," and other forms thereof, are intended to be equivalent in meaning and be open ended. Put another way, an item or items following any one of these words is not meant to be an exhaustive listing of such item or items, or meant to be limited to only the listed item or items.

Also, as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred systems and methods are now described.

An embodiment of the present invention relates to a material and apparel that positively affect the health and wellbeing of a mammal.

FIG. 1 illustrates a Table 1 that shows different compositions used for preparing apparel 101 in accordance with an embodiment of the invention.

Part I—Formation of Material and Apparel

In accordance with an embodiment of the present invention, the materials of the present inventions include therapeutic wraps, bandages, apparel or clothing, patch having therapeutic applications. The materials are nonsterile, tubular, elastic in nature and intended to be worn externally on the body to provide support or local pressure for various health- and wellbeing-promoting purposes, including therapeutic and preventive ones, while also enabling movement.

In accordance with an embodiment of the present invention, the materials and apparel include at least one fiber that includes with a semiconductor in desired proportions. When the materials and apparel include fibers, they are formed as knitted fabric made of the fibers. The fiber or fibers of the materials may include a thermoplastic material selected from the groups consisting of: Polyester, regular Polyethylene Terephalate, Cationic Dyeable Polyethylene Terephalate, High Tenacity Polyethylene, Fire Retardant Polyethylene Terephalate and Polyurethane, Polytrimethylene Terephalate, Polybutylene Terephalate, Nylon, Acrylic and Modacrylic. The material may include an artificial regenerated cellulosic material selected from the groups consisting of: Rayon, High Wet Modulus Rayon, Modal and Lyocell.

The fabric blends of the materials and apparel may include Carbonized Charcoal, Cotton, Cotton (Germanium Infused), Cotton (Germanium/Carbonized Charcoal Infused), Germanium/Bamboo Charcoal Fiber, Polyester (Carbonized Charcoal Infused), Polyester, Polyester (Germanium/Carbonized Charcoal Infused), Polyester (Germanium Infused), Nylon (Germanium Infused) Nylon, Spandex, Rubber, Viscose, Wool fiber. The materials may further include spandex, rubber, viscose or other elastic fibers to provide additional stretch ability and resilience.

The fiber or fibers include a semiconductor that includes germanium. The germanium can be formed as a powder of nanoparticles that is doped or otherwise combined into a first material formed of cotton, nylon or polyester. The semiconductor-combined fabric is then combined with other threads of fiber to create yarn.

Germanium is a nontoxic semiconductor metalloid located between tin and silicone in the periodic table and has been widely used in electronics and optics, though not in fibers and apparel. A semiconductor such as germanium differs from metals in that as the temperature of semiconductors increases, their resistance decreases. This is a result of germanium having more "free" electrons at certain temperatures, allowing for a higher conductivity. Embedding germanium into apparel is an effective way to use a transdermal effect to create a micro-electromagnetic field. As described further below, that micro-electromagnetic field leads to positive effects on the wellbeing of mammals, including humans by, for example, increasing circulation and reducing or otherwise positively affecting the inflammatory process.

The materials and apparel of the present inventions are made of knitted fabric formed of fibers. As used herein, the term "fiber" means a thread, filament or yarn as long as it can be used to formed a knitted, woven, or other form of fabric. Both natural and synthetic fibers are usable. Usable natural fibers include cellulose, and synthetic fibers include polyamide, polyester or polyolefin, or nylon. The apparel fabric may further include spandex, rubber, viscose or other elastic fibers to provide additional stretch ability and resilience.

The materials and apparel may also be prepared using a nanocarbon charcoal doped into the fibers of cotton, nylon or polyester manufactured in a closed loop process and then spun into a yarn. The fiber yarn is then woven into knitted fabrics, and added to other fiber thread to create double- or triple-fiber thread yarn. The carbonized charcoal fiber is manufactured by a Taiwanese-grown bamboo (preferably 4 to 5 year old), is dried and burned in 800-1200 degree C. in an oven until it is reduced to charcoal, it is then ground and filtered into nano-particles which are doped into the fibers then spun into a yarn. The fiber yarn is then woven into knitted fabrics, and added to other fiber thread to create double- or triple-fiber thread yarn.

The material and the apparel may also be prepared using carbonized charcoal fibers infused with a semiconductor, such as germanium. The carbonized charcoal fibers generally have a titer of 0.5 to 20, in particular 1 to 5, dtex. The titer of the textile fibers is usually in the same range. The mixture of the carbonized charcoal fibers with the textile staple fibers can be spun into mixed yarns in a known manner and these, in turn, can be easily interwoven. The mixed yarn containing the carbonized charcoal fibers can be used either only in the weft, only in the warp, or both in the warp and weft, depending on the intended use of the apparel.

If a purely textile yarn is used for warp or weft, it does not have to be made of the same material as the staple fibers of the mixed yarn, but can be adapted to the particular purpose of the said material and said apparel.

The materials and the apparel may be prepared in many different ways, depending on the base material that is used to make the apparel. For example, if apparel is made of an elastic polymeric material, a seamless tubular material may be extruded from an extrusion machine. The tubular material is then cut into an appropriate length to produce a sleeve suitable for enclosing a body portion. The perforated section may be produced in a mid-section of the extruded tubular material by burning holes (e.g., via laser), or by punching holes mechanically (e.g., needle-punching). The medicinal section may be incorporated using a suitable material such as foam, pads or fabric.

The materials and apparel may include carefully selected portions being formed to reduce swelling, pain or to provide fast healing of a wound. Those materials and apparel may be used to reduce pain or swelling, increase circulation, upon contact with the region of the body of the mammal, for example arthritis, diabetes, impact injuries, neuropathy, sprains, strains, tendonitis, vascular conditions, muscle fatigue, edema, and repetitive stress injuries, lymphedema, phlebitis, varicose veins, post-burn treatment, post-fracture and injury (including sports injury such as a pulled muscle) edema, stasis ulcers, obesity and circulatory disorders.

The materials and apparel may be prepared using conventional methods which involve milling the raw materials followed by heating and grinding them into nanoparticles and then doping into fibers formed of the raw materials.

For upper-body human applications, the apparel of the inventions may include a wrist sleeve, arm sleeve, shoulder brace, bandage wrap, back brace, circulation gloves and/or beanies. For lower-body human application, the apparel of the inventions may include an ankle sleeve, calf sleeve, knee sleeve, leg sleeve, boot sleeve, hip brace. Asymmetrically-positioned material construction may also be applied in the apparel covering both a portion of the upper and lower body of a wearer (e.g., jumpsuits). The apparel may be designed to be loose-fitting, "close-to-body" or snug-fitting, or even compression-fitting.

The apparel may also be nonsterile, tubular, elastic support sleeves intended to be worn on the body to provide support or local pressure for various therapeutic/preventive purposes while enabling movement. By referring to the body or a body portion, those phrases mean the body of a mammal, including a human. However, support or compression are surprisingly not required for the materials and apparel of the inventions to cause their health- and wellbeing-promoting effects.

The materials and apparel are made of any suitable material as long as it can enclose or be stretched to fit a body portion. If stretching is required, the materials and apparel must have sufficient elasticity to contact the skin and to stay on the body portion. For example, it may be an elastic polymeric material, a woven, non-woven or knitted fabric, or any combinations thereof. Preferably, the apparel is generally tubular or cylindrical in shape and is made of a knitted fabric. More preferably, the apparel is a seamless, circularly knitted sleeve so that it does not create any undesired crease on the skin when the apparel is worn for a prolonged period of time.

The materials and apparel of the present inventions may be made of a knitted fabric and may be produced using a suitable automatic weaving machine.

Part II—Health- and Wellbeing-Promoting Effects

The materials and apparel may be specifically designed to achieve the various above-referenced effects, such as reducing pain or swelling, thereby promoting the health and wellbeing of the wearer. These materials or apparel may, for example, include a first material combined with a second material.

For the above-referenced effect that causes an external mid-IR optical wave to be received by the body, the mid-infrared (mid-IR) spectral region, which spans 3-30 µm, is a rich region for medical research and instrumentation. This is because many important biomolecules, such as proteins, lipids, and amides, contains strong characteristic vibrational transitions and the region contains two atmospheric transmission windows of 3-5 µm and 8-13 µm that are useful for free space communication. Due to the unique specificity of a biological molecule's spectrum in the mid-IR, lasers in this wavelength regime have a unique advantage over ultraviolet (UV) and visible or near-IR lasers. Common mid-IR emitters for biomedical applications include $CO_2$ lasers; free electron lasers (FELs), optical parametric oscillators (OPOs), fiber lasers and semiconductor laser diodes.

For the above-referenced effect that pertains to promoting thermoregulation of the body, ultrasound is used to evaluate several joints at the same time, including functional assessments. Further, ultrasound is used to visualize pathophysiological changes such as synovitis, tenosynovitis, enthesitis, bone erosions, and crystal deposits at a subclinical level to identify and differentiate most common types of inflammatory arthritis.

Depending on the temperature gradients, the effects from ultrasound exposure includes mild heating, coagulative necrosis, tissue vaporization, or all three. Ultrasonic cavitation and gas body activation are closely related mechanisms which depend on the rarefactional pressure amplitude of ultrasound waves.

Embodiments of the inventions are further described by referring to the drawings. As with the textual description, the drawings are merely illustrative of embodiments of the invention and are not meant to limit the scope of the present invention in any way. To refer to the materials and apparel of the inventions, the phrase material/apparel is used.

FIG. 2 shows a human arm 100 covered by material/apparel 101 worn by a wearer which upon contact 102 with the region of the wearer causes a decrease in the swelling or reduces pain or helps in blood circulation, in accordance with an embodiment of the invention.

In accordance with an embodiment of the present invention, material 101 for contacting the mammal with the body that includes a region that is experiencing swelling. An expanse of material 101 is formed with a semiconductor and constructed for contact 102 with that region, and contact 102 causes the decrease in the swelling.

In accordance with an embodiment of the present invention, the expanse is constructed for contact 102 with skin 103 of the mammal. Further, the semiconductor is germanium. Further, the expanse, upon contact 102 with the region of the body, eliminates the swelling. Further, the expanse is formed as a geometric shape. The expanse is formed so that it has to be worn by the mammal. Further, the mammal is a human.

In accordance with another embodiment of the present invention, the present inventions relate to apparel 101 for the human whose body includes a region that is experiencing swelling. Apparel 101 includes a wearable form that is made of a semiconductor and constructed for contact with an outer region of the mammal when the mammal wears apparel 101. Upon contact 102 with that, apparel 101 causes a decrease in the swelling.

In accordance with an embodiment of the present invention, when material/apparel 101 is placed on the body part, a compressive force or support is then applied to the body part for a sufficient amount of time to mitigate swelling in the limb. Because human skin 103 is elastic in nature, when systems such as the lymphatic or venous return systems fail to function properly, the limb or body part accumulates fluid and stretches to accommodate edema.

In accordance with an embodiment of the present invention, the form is made for contact 102 with skin 103 of the human body. Further, the semiconductor is germanium. Further, the form, upon contact 102 with the region of the human body, eliminates the swelling. The form is made as one of the groups consisting of a shirt, pants, dress, underwear, clothing, and a sleeve.

Figure 3:
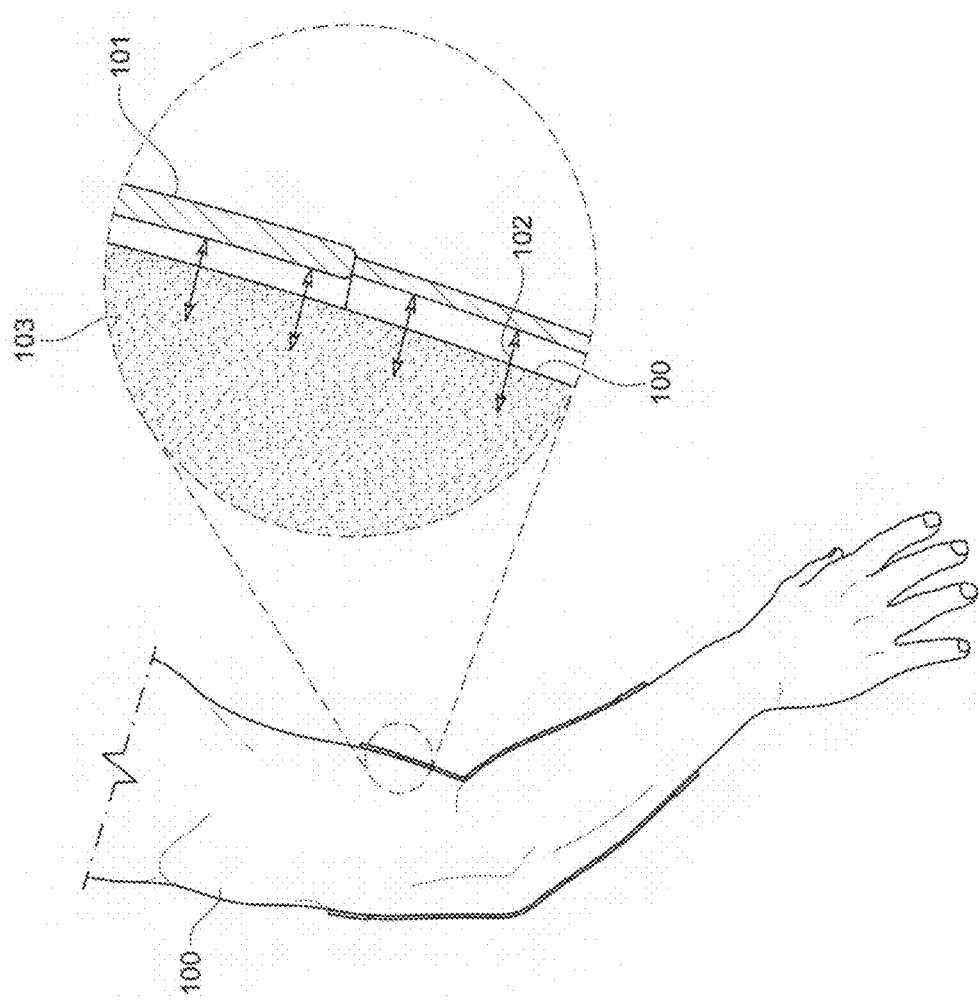
FIG. 3 shows a side-sectional view of arm 100 showing contact 102 of the bottom surface of material/apparel 101 with top surface (skin) 103 of arm 100 in accordance with an embodiment of the invention.

FIG. 3 shows a side-sectional view of the arm showing contact 102 of the bottom surface of material/apparel 101 with the top surface (skin) of arm 100 in accordance with an embodiment of the invention.

Figure 4:
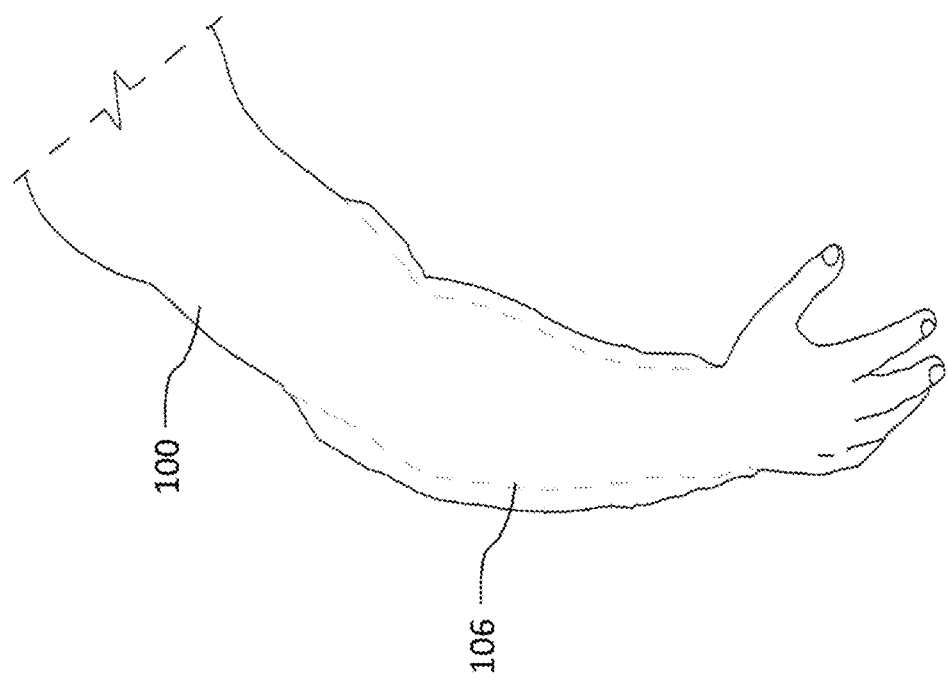
FIG. 4 shows a side-sectional view of a swollen arm 106, in accordance with an embodiment of the invention.

FIG. 4 shows a side-sectional view of a swollen arm 106, in accordance with an embodiment of the invention.

Figure 5:
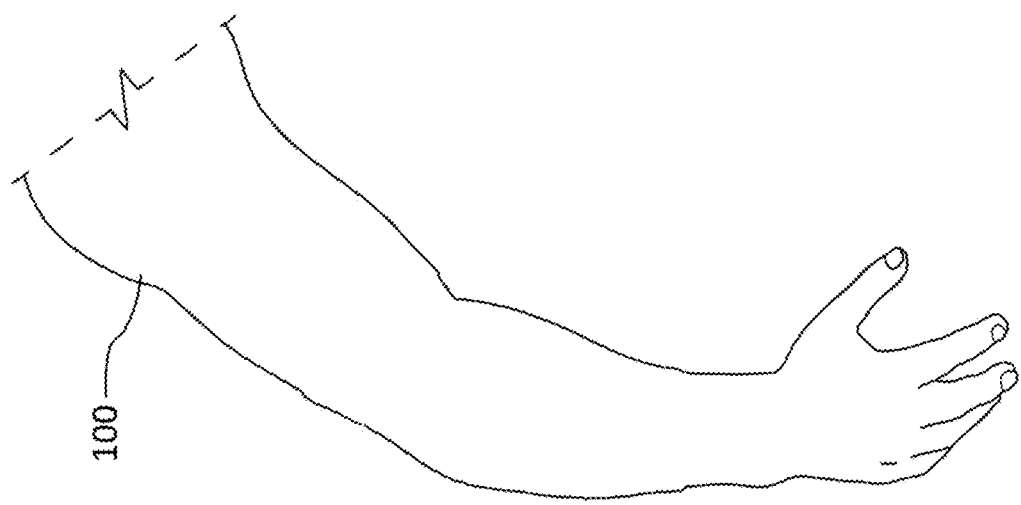
FIG. 5 shows a normal state (swelling reduced) of swollen arm 106, in accordance with an embodiment of the invention.

FIG. 5 shows a normal state (swelling reduced) of swollen arm 106, in accordance with an embodiment of the invention.

In accordance with an embodiment of the present invention, material/apparel 101 upon contact 102 with skin 103 (top surface of the body) results in decrease in pain or swelling, increase in circulation and causing the wound to heal faster.

Figure 6:
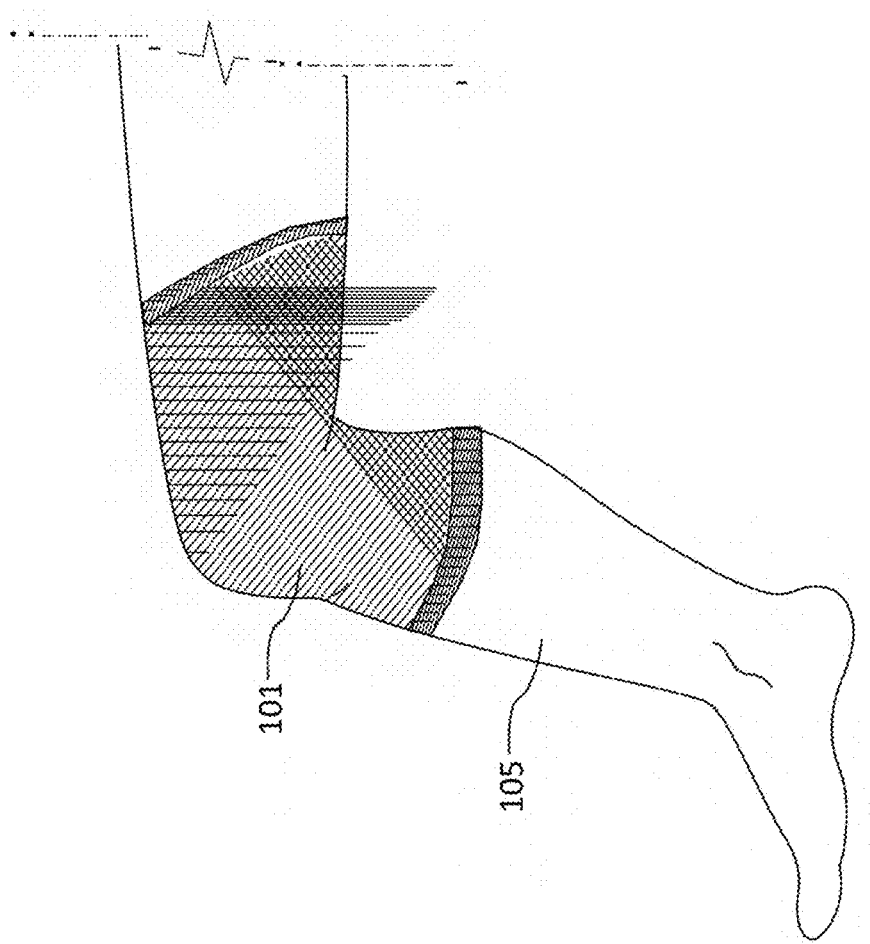
FIG. 6 show a right leg sleeve 105 like arm 100 one in FIG. 2 (covering knee and extending from the lower thigh to the upper calf), in accordance with an embodiment of the invention.

FIG. 6 show a right leg sleeve 105 like arm 100 one in FIG. 2 (covering knee and extending from the lower thigh to the upper calf), in accordance with an embodiment of the invention.

In accordance with an embodiment of the present invention, the present inventions relate to material 101 for contacting the mammal with the body that includes a region that has a wound that requires a first time to heal fully. An expanse is formed with a semiconductor and constructed for contact 102 with that region and contact 102 causes the wound to heal in a second time that is less than the first time.

In accordance with an embodiment of the present invention, the expanse is constructed for contact 102 with skin 103 of the mammal. Further, the semiconductor is germanium. Further, the expanse, upon contact 102 with the region of the body, eliminates the swelling. Further, the expanse is formed as a geometric shape. The expanse is formed so that it has to be worn by the mammal. Further, the mammal is a human.

In accordance with another embodiment of the present invention, the present inventions relate to apparel 101 for a human whose body includes a region that has a wound that requires a first time to heal fully. Apparel 101 includes a wearable form that is made of a semiconductor and constructed for contact 102 with an outer region of a mammal when the mammal wears apparel 101. Upon contact 102 with that, apparel 101 causes the wound to heal in a second time that is less than the first time.

In accordance with an embodiment of the present invention, the form is made for contact 102 with skin 103 of the human body. Further, the semiconductor is germanium. Further, the form, upon contact 102 with the region of the human body, eliminates the swelling. The form is made as one of the groups consisting of a shirt, pants, dress, underwear, clothing, and a sleeve.

In accordance with an embodiment of the present invention, the present inventions relate to material 101 for contacting the mammal with the body that includes a region that has a wound that requires a first time for the body to recover fully. An expanse is formed with a semiconductor and constructed for contact 102 with that region and contact 102 causes the body to recover in a second time that is less than the first time.

In accordance with an embodiment of the present invention, the expanse is constructed for contact 102 with skin 103 of the mammal. Further, the semiconductor is germanium. Further, the expanse, upon contact 102 with the region of the body, eliminates the swelling. Further, the expanse is formed as a geometric shape. The expanse is formed so that it has to be worn by the mammal. Further, the mammal is a human.

In accordance with another embodiment of the present invention, the present inventions relate to apparel 101 for a human whose body includes a region that has a wound that requires a first time for the body to recover fully. Apparel 101 includes a wearable form that is made of a semiconductor and constructed for contact 102 with an outer region of a mammal when the mammal wears apparel 101. Upon contact 102 with that, apparel 101 causes the body to recover in a second time that is less than the first time.

In accordance with an embodiment of the present invention, the form is made for contact 102 with skin 103 of the human body. Further, the semiconductor is germanium. Further, the form, upon contact 102 with the region of the human body, eliminates the swelling. The form is made as one of the groups consisting of a shirt, pants, dress, underwear, clothing, and a sleeve.

Figure 7:
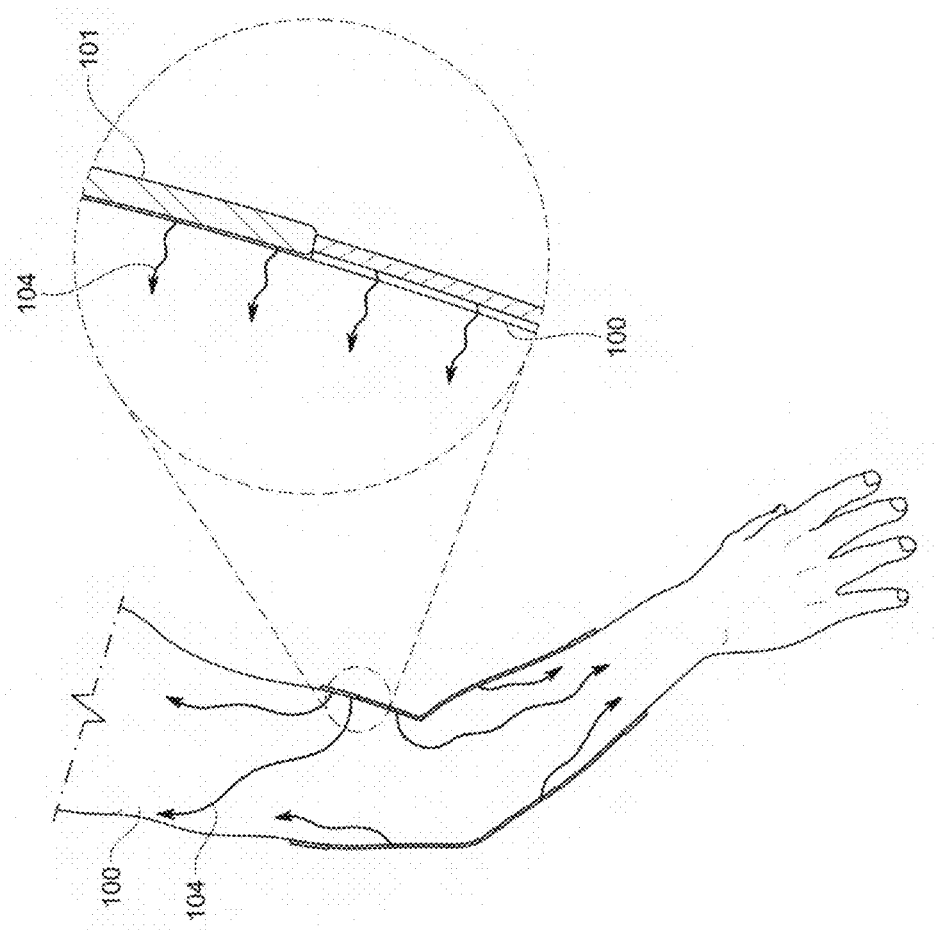
FIG. 7 shows an enlarged, fragmentary view of FIG. 3 showing how the material/apparel 101 of the invention sends external mid-IR optical waves 104 to arm 100 through a skin 103 by contacting it, in accordance with an embodiment of the invention.

FIG. 7 shows an enlarged, fragmentary view of FIG. 3 showing how the material/apparel 101 of the invention sends external mid-IR optical waves 104 to arm 100 through a skin 103 by contacting it, in accordance with an embodiment of the invention.

Figure 8:
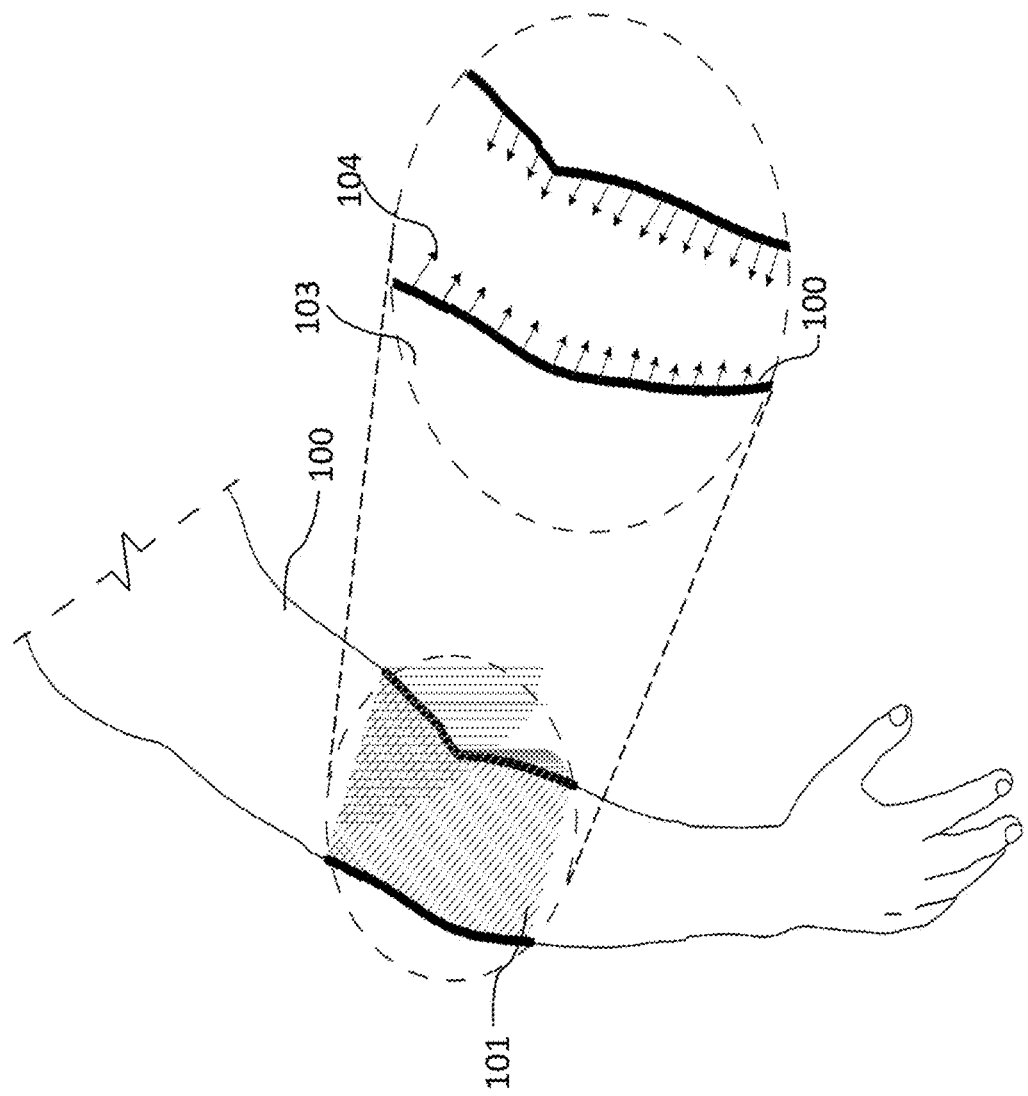
FIG. 8 shows the mid-IR optical wave 104 being transmitted from the sleeve to arm 100, in accordance with an embodiment of the invention.

FIG. 8 shows mid-IR optical wave 104 being transmitted from the sleeve to arm 100, in accordance with an embodiment of the invention.

In accordance with an embodiment of the present invention, the present inventions relate to material 101 for contacting the mammal with the body that is capable of receiving external optical waves 104. An expanse is formed with a semiconductor and constructed for contact 102 with that region and contact 102 causes external mid-IR optical wave 104 to be received by the body.

In accordance with an embodiment of the present invention, the expanse is constructed for contact 102 with skin 103 of the mammal. Further, the semiconductor is germanium. Further, the expanse, upon contact 102 with the region of the body, eliminates the swelling. Further, the expanse is formed as a geometric shape. The expanse is formed so that it has to be worn by the mammal. Further, the mammal is a human.

In accordance with another embodiment of the present invention, the present inventions relate to apparel 101 for a human whose body is capable of receiving optical wave 104. Apparel 101 includes a wearable form that is made of a semiconductor and constructed for contact 102 with an outer region of a mammal when the mammal wears apparel 101. Upon contact 102 with that, apparel 101 causes external mid-IR optical wave 104 to be received by the body.

In accordance with an embodiment of the present invention, the form is made for contact 102 with skin 103 of the human body. Further, the semiconductor is germanium. Further, the form, upon contact 102 with the region of the human body, eliminates the swelling. The form is made as one of the groups consisting of a shirt, pants, dress, underwear, clothing, and a sleeve.

In accordance with an embodiment of the present invention, when material/apparel 101 is placed on the body part, external mid-IR optical wave 104 penetrates the body's soft tissue where inflammation occurs in the body. External mid-IR optical wave 104 helps in expanding blood vessels and increases circulation so more oxygen reaches an injured area of the body. This reduces pain and increases the speed of the healing process.

In accordance with another embodiment of the present invention, when external mid-IR optical wave 104 is used with the combination of a far infrared wave, external mid-IR optical wave 104 effectively stimulates the cardiovascular system and raises body temperature. This also helps in the speedy recovery of the body part where external mid-IR optical wave 104 is applied.

Figure 9:
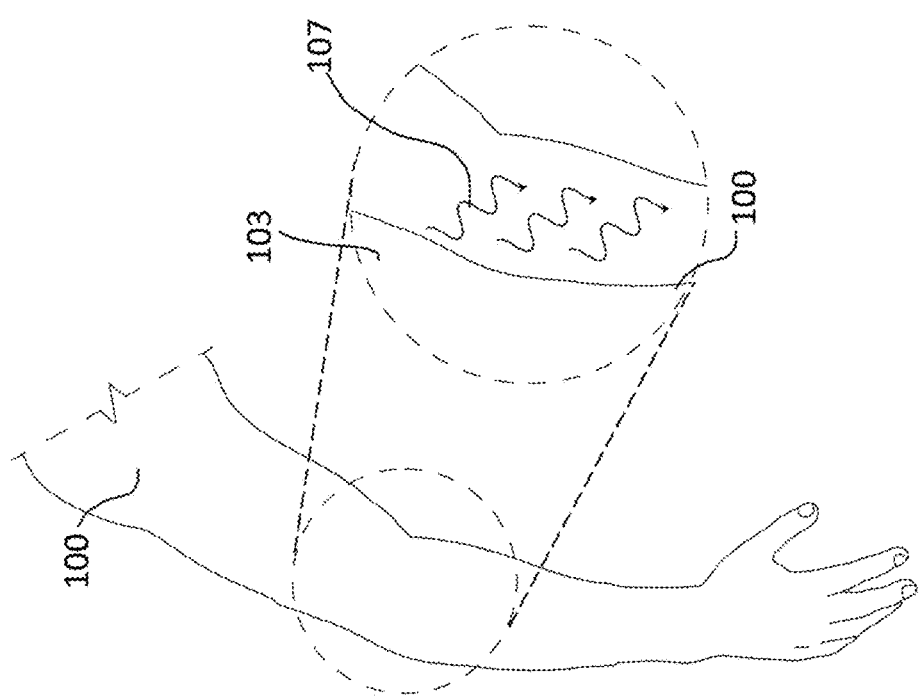
FIG. 9 shows an enlarged section of the forearm that depicts cellular movement at a first speed/rate 107 in accordance with an embodiment of the invention.

FIG. 9 shows an enlarged section of the forearm that depicts cellular movement at a first speed/rate 107 in accordance with an embodiment of the invention.

Figure 10:
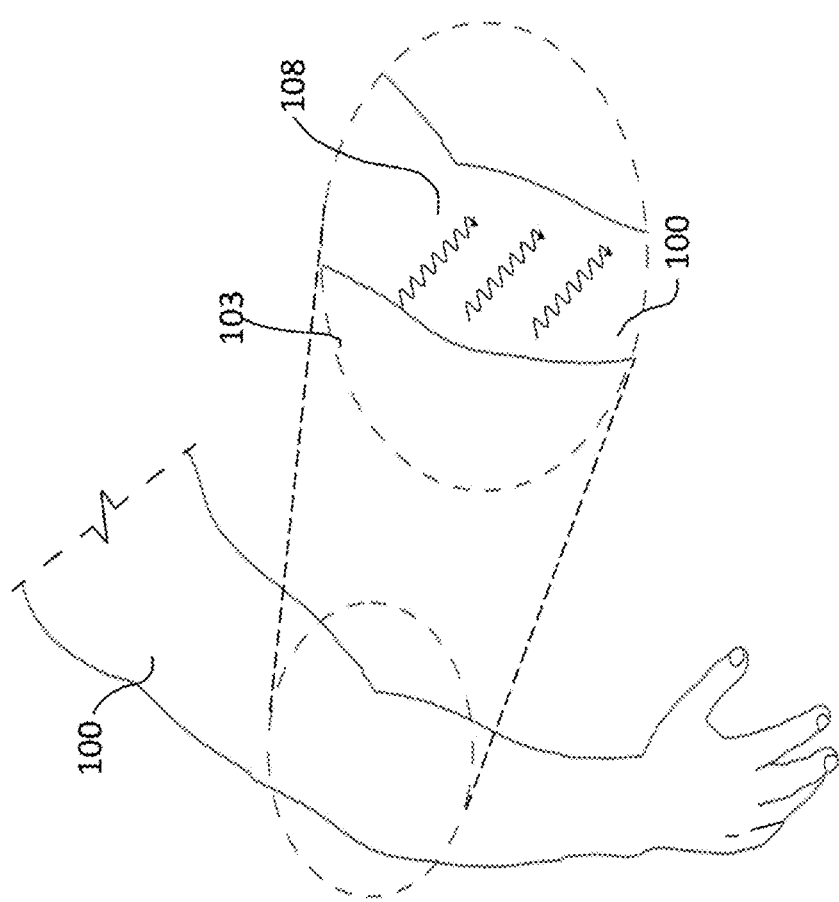
FIG. 10 shows the enlarged section of the forearm that depicts cellular movement at a second speed/rate 108 in accordance with an embodiment of the invention.

FIG. 10 shows the enlarged section of the forearm that depicts cellular movement at a second speed/rate 108 in accordance with an embodiment of the invention.

In accordance with an embodiment of the present invention, the present inventions relate to material 101 for contacting the mammal with the body that includes mobile cells that move within the body and exhibit cellular movement at first rate 107. An expanse is formed with a semiconductor and constructed for contact 102 with that region and contact 102 causes the cellular movement to occur at second rate 108 that is greater than first rate 107.

In accordance with an embodiment of the present invention, the expanse is constructed for contact 102 with skin 103 of the mammal. Further, the semiconductor is germanium. Further, the expanse, upon contact 102 with the region of the body, eliminates the swelling. Further, the expanse is formed as a geometric shape. The expanse is formed so that it has to be worn by the mammal. Further, the mammal is a human.

In accordance with another embodiment of the present invention, the present inventions relate to apparel 101 for a human whose body includes mobile cells that move within the body and exhibit cellular movement at first rate 107. Apparel 101 includes a wearable form that is made of a semiconductor and constructed for contact 102 with an outer region of a mammal when the mammal wears apparel 101. Upon contact 102 with that, apparel 101 causes the cellular movement to occur at second rate 108 that is greater than first rate 107.

In accordance with an embodiment of the present invention, the form is made for contact 102 with skin 103 of the human body. Further, the semiconductor is germanium. Further, the form, upon contact 102 with the region of the human body, eliminates the swelling. The form is made as one of the groups consisting of a shirt, pants, dress, underwear, clothing, and a sleeve.

In accordance with an embodiment of the present invention, when material/apparel 101 is placed on the body part, cellular movement occurs in a body at second rate 108 that is greater than the first rate 107 to suppress inflammation and edema-induced pain, by reducing the inflammatory mediator release, and by edema reduction.

In accordance with an embodiment of the present invention, the present inventions relate to material 101 for contacting the mammal with the skin-covered, tissue-containing body that is capable of experiencing temperature changes in spite of being warm-blooded. An expanse is formed with a semiconductor and constructed for contact 102 with that region and contact 102 promotes thermoregulation of the body by cooling the body when it exceeds a first temperature and heating it when it falls below a second temperature.

In accordance with an embodiment of the present invention, the expanse, upon contact 102 with the region of the body, promotes thermoregulation by cooling the body when it exceeds the first temperature, and heating it when it falls below the second temperature. The expanse is constructed for contact 102 with skin 103 of the mammal. Further, the semiconductor is germanium. Further, the expanse, upon contact 102 with the region of the body, causes thermoregulation of the body. Further, the expanse is formed as a geometric shape. The expanse is formed so that it has to be worn by the mammal. Further, the mammal is a human.

In accordance with another embodiment of the present invention, the present inventions relate to apparel 101 for a human whose skin-covered, tissue-containing body is capable of experiencing temperature changes in spite of being warm-blooded. Apparel 101 includes a wearable form that is made of a semiconductor and constructed for contact 102 with an outer region of a mammal when the mammal wears apparel 101. Upon contact 102 with that, apparel 101 promotes thermoregulation of the body.

In accordance with an embodiment of the present invention, the form, upon contact 102 with the region of the body, promotes thermoregulation by cooling the body when it exceeds a first temperature, and heating it when it falls below a second temperature. The form is made for contact 102 with skin 103 of the human body. Further, the semiconductor is germanium. Further, the form, upon contact 102 with skin 103, causes thermoregulation. The form is made as one of the groups consisting of a shirt, pants, dress, underwear, clothing, and a sleeve.

In accordance with an embodiment of the present invention, the present inventions relate to material 101 for contacting the mammal with the body that has arthritis, experiences pain, and has decreased physical capabilities due to the arthritis. An expanse is formed with a semiconductor and constructed for contact 102 with that region and contact 102 treats the arthritis by reducing pain and improving physical capabilities chosen from the groups consisting of grip and range of motion.

In accordance with an embodiment of the present invention, the expanse is constructed for contact 102 with skin 103 of the mammal. Further, the semiconductor is germanium. Further, the expanse is formed as a geometric shape. The expanse is formed so that it has to be worn by the mammal. Further, the mammal is a human.

In accordance with another embodiment of the present invention, the present inventions relate to apparel 101 for a human whose body has arthritis, experiences pain, and has decreased physical capabilities due to the arthritis. Apparel 101 includes a wearable form that is made of a semiconductor and constructed for contact 102 with an outer region of a mammal when the mammal wears apparel 101. Upon contact 102 with that, apparel 101 treats the arthritis by reducing pain and improving physical capabilities chosen from the groups consisting of grip and range of motion.

In accordance with an embodiment of the present invention, the form is made for contact 102 with skin 103 of the human body. Further, the semiconductor is germanium. The form is made as one of the groups consisting of a shirt, pants, dress, underwear, clothing, and a sleeve.

In accordance with an embodiment of the present invention, when material/apparel 101 is placed on the body part, it may reduce pain by shifting human weight off the most damaged portion of the knee. Wearing material/apparel 101 helps in improving the human ability to get around and helps them walk farther comfortably.

In accordance with an embodiment of the present invention, the present inventions relate to material 101 for contacting the human with the body that is capable of playing sports and getting sports injuries. An expanse is formed with a semiconductor and constructed for contact 102 with that region and contact 102 tends to prevent sports injuries.

In accordance with an embodiment of the present invention, the expanse is constructed for contact 102 with skin 103 of the mammal. Further, the semiconductor is germanium. Further, the expanse, upon contact 102 with the region of the body, prevents sports injuries. Further, the expanse is formed as a geometric shape. The expanse is formed so that it has to be worn by the mammal. Further, the mammal is a human.

In accordance with another embodiment of the present invention, the present inventions relate to apparel 101 for a human with a body that is capable of playing sports and getting sports injuries. Apparel 101 includes a wearable form that is made of a semiconductor and constructed for contact 102 with an outer region of a mammal when the mammal wears apparel 101. Upon contact 102 with that, apparel 101 tends to prevent sports injuries.

In accordance with an embodiment of the present invention, the form is made for contact 102 with skin 103 of the human body. Further, the semiconductor is germanium. Further, the form, upon contact 102 with the region of the human body, prevents sports injuries. The form is made as one of the groups consisting of a shirt, pants, dress, underwear, clothing, and a sleeve.

In accordance with an exemplary embodiment of the present invention, material/apparel 101 is designed to offer protection to the human body part. When material/apparel 101 is placed on the body part, it creates an inside and outside pressure on the body part. This inside and outside pressure act to stabilize the human body and reduce the stress it receives when playing sports. This is how material/apparel 101 may help to protect against sport injuries during playing sports.

In accordance with an embodiment of the present invention, the present inventions relate to material 101 for contacting the human with the body that has a neurological system, tissue, and blood that includes nutrient-containing hemoglobin, and the tissue is capable of being oxygenated and receiving nutrients by the hemoglobin in the blood that flows through the tissue. An expanse is formed with a semiconductor and constructed for contact 102 with that region and contact 102 tends to decrease neuropathy in the body by increasing the flow of hemoglobin-containing blood through the tissue.

In accordance with an embodiment of the present invention, the expanse, upon contact 102 with the region of the body, tends to decrease neuropathy by increasing the flow of hemoglobin-containing blood through the tissue. The expanse is constructed for contact 102 with skin 103 of the mammal. Further, the semiconductor is germanium. Further, the expanse is formed as a geometric shape. The expanse is formed so that it has to be worn by the mammal. Further, the mammal is a human.

In accordance with another embodiment of the present invention, the present inventions relate to apparel 101 for a human with a body that has a neurological system, tissue, and blood that includes nutrient-containing hemoglobin, and the tissue is capable of being oxygenated and receiving nutrients by the hemoglobin in the blood that flows through the tissue. Apparel 101 includes a wearable form that is made of a semiconductor and constructed for contact 102 with an outer region of a mammal when the mammal wears apparel 101. Upon contact 102 with that, apparel 101 tends to decrease neuropathy in the body by increasing the flow of hemoglobin-containing blood through the tissue.

In accordance with an embodiment of the present invention, the form, upon contact 102 with the region of the body, tends to decrease neuropathy by increasing the flow of hemoglobin-containing blood through the tissue. The form is made for contact 102 with skin 103 of the human body. Further, the semiconductor is germanium. Further, the form, upon contact 102 with the region of the human body, eliminates the swelling. The form is made as one of the groups consisting of a shirt, pants, dress, underwear, clothing, and a sleeve.

In accordance with an embodiment of the present invention, the present inventions relate to material 101 for contacting the human with the body that has cognitive function and is capable of experiencing a concussion that causes headaches. An expanse is formed with a semiconductor and constructed for contact 102 with that region and contact 102 tends to promote healing after a concussion. That contact 102 promotes healing after the concussion by restoring cognitive function and, as a result, tends to reduce headaches.

In accordance with an embodiment of the present invention, the expanse is constructed for contact 102 with skin 103 of the mammal. The expanse, upon contact 102 with the region of the body, tends to promote healing after the concussion by restoring cognitive function and, as a result, tends to reduce headaches. Further, the semiconductor is germanium. Further, the expanse is formed as a geometric shape. The expanse is formed so that it has to be worn by the mammal. Further, the mammal is a human.

In accordance with another embodiment of the present invention, the present inventions relate to apparel 101 for a human with a body that has cognitive function and is capable of experiencing a concussion that causes headaches. Apparel 101 includes a wearable form that is made of a semiconductor and constructed for contact 102 with an outer region of a mammal when the mammal wears apparel 101. Upon contact 102 with that, apparel 101 tends to promote healing after a concussion by restoring cognitive function and, as a result, tends to reduce headaches.

In accordance with an embodiment of the present invention, the form is made for contact 102 with skin 103 of the human body. The form, upon contact 102 with the region of the body, tends to promote healing after the concussion by restoring cognitive function and, as a result, tends to reduce headaches. Further, the semiconductor is germanium. The form is made as one of the groups consisting of a shirt, pants, dress, underwear, clothing, and a sleeve.

In accordance with an embodiment of the present invention, the present inventions relate to material 101 for contacting the human with the body that is capable of experiencing headaches. An expanse is formed with a semiconductor and constructed for contact 102 with that region and contact 102 tends to reduce headaches.

In accordance with an embodiment of the present invention, the expanse is constructed for contact 102 with skin 103 of the mammal. The expanse, upon contact 102 with the region of the body, tends to eliminate headaches. Further, the semiconductor is germanium. Further, the expanse is formed as a geometric shape. The expanse is formed so that it has to be worn by the mammal. Further, the mammal is a human.

In accordance with another embodiment of the present invention, the present inventions relate to apparel 101 for a human with a body that is capable of experiencing headaches. Apparel 101 includes a wearable form that is made of a semiconductor and constructed for contact 102 with an outer region of a mammal when the mammal wears apparel 101. Upon contact 102 with that, apparel 101 tends to reduce headaches.

In accordance with an embodiment of the present invention, the form is made for contact 102 with skin 103 of the human body. The form, upon contact 102 with the region of the body, tends to eliminate headaches. Further, the semiconductor is germanium. The form is made as one of the groups consisting of a shirt, pants, dress, underwear, clothing, and a sleeve.

In accordance with an embodiment of the present invention, the present inventions relate to material 101 for contacting the human with the body that contains positive ions. An expanse is formed with a semiconductor and constructed for contact 102 with that region. That contact 102 releases negative ions that enter the body and pair with the positive ions, causing an exothermic reaction that cools the body adjacent the region where the pairing of negative ions and positive ions occurs.

In accordance with an embodiment of the present invention, the expanse is constructed for contact 102 with skin 103 of the mammal. Further, the semiconductor is germanium. Further, the expanse is formed as a geometric shape. The expanse is formed so that it has to be worn by the mammal. Further, the mammal is a human.

In accordance with another embodiment of the present invention, the present inventions relate to apparel 101 for a human with a body that contains positive ions. Apparel 101 includes a wearable form that is made of a semiconductor and constructed for contact 102 with an outer region of a mammal when the mammal wears apparel 101. Upon contact 102 with that, apparel 101 releases negative ions that enter the body and pair with the positive ions, causing an exothermic reaction that cools the body adjacent the region where the pairing of negative ions and positive ions occurs.

In accordance with an embodiment of the present invention, the form is made for contact 102 with skin 103 of the human body. Further, the semiconductor is germanium. The form is made as one of the groups consisting of a shirt, pants, dress, underwear, clothing, and a sleeve.

In accordance with an embodiment of the present invention, the present inventions relate to material 101 for contacting the human with the body that is capable of experiencing muscle load. An expanse is formed with a semiconductor and constructed for contact 102 with that region and contact 102 tends to decrease muscle load in the body.

In accordance with an embodiment of the present invention, the expanse is constructed for contact 102 with skin 103 of the mammal. Further, the semiconductor is germanium. Further, the expanse is formed as a geometric shape. The expanse is formed so that it has to be worn by the mammal. Further, the mammal is a human.

In accordance with another embodiment of the present invention, the present inventions relate to apparel 101 for a human with a body that is capable of experiencing muscle load. Apparel 101 includes a wearable form that is made of a semiconductor and constructed for contact 102 with an outer region of a mammal when the mammal wears apparel 101. Upon contact 102 with that, apparel 101 tends to decrease muscle load in the body.

In accordance with an embodiment of the present invention, the form is made for contact 102 with skin 103 of the human body. Further, the semiconductor is germanium. The form is made as one of the groups consisting of a shirt, pants, dress, underwear, clothing, and a sleeve.

In accordance with an embodiment of the present invention, the present inventions relate to material 101 for contacting the human with the body that includes tissue, blood vessels and cells, and in which there is interstitial fluid pressure that relates to interstitial fluid that is extracellular and outside of blood vessels. An expanse is formed with a semiconductor and constructed for contact 102 with that region and contact 102 tends to increase the interstitial fluid pressure in the body.

In accordance with an embodiment of the present invention, the expanse is constructed for contact 102 with skin 103 of the mammal. Further, the semiconductor is germanium. Further, the expanse is formed as a geometric shape. The expanse is formed so that it has to be worn by the mammal. Further, the mammal is a human.

In accordance with another embodiment of the present invention, the present inventions relate to apparel 101 for a human with a body that includes tissue, blood vessels and cells, and in which there is interstitial fluid pressure that relates to interstitial fluid that is extracellular and outside of blood vessels. Apparel 101 includes a wearable form that is made of a semiconductor and constructed for contact 102 with an outer region of a mammal when the mammal wears apparel 101. Upon contact 102 with that, apparel 101 tends to increase the interstitial fluid pressure in the body.

In accordance with an embodiment of the present invention, the form is made for contact 102 with skin 103 of the human body. Further, the semiconductor is germanium. The form is made as one of the groups consisting of a shirt, pants, dress, underwear, clothing, and a sleeve.

In accordance with an embodiment of the present invention, the present inventions relate to material 101 for contacting the human with the body that includes a brain, sensory receptors, muscles, and a proprioception system. An expanse is formed with a semiconductor and constructed for contact 102 with that region and contact 102 tends to balance the muscles in the body by creating a proprioceptive response within the proprioception system.

In accordance with an embodiment of the present invention, the expanse is constructed for contact 102 with skin 103 of the mammal. Further, the semiconductor is germanium. Further, the expanse is formed as a geometric shape. The expanse is formed so that it has to be worn by the mammal. Further, the mammal is a human.

In accordance with another embodiment of the present invention, the present inventions relate to apparel 101 for a human with a body that includes a brain, sensory receptors, muscles, and a proprioception system. Apparel 101 includes a wearable form that is made of a semiconductor and constructed for contact 102 with an outer region of a mammal when the mammal wears apparel 101. Upon contact 102 with that, apparel 101 tends to balance the muscles in the body by creating a proprioceptive response within the proprioception system.

In accordance with an embodiment of the present invention, the form is made for contact 102 with skin 103 of the human body. Further, the semiconductor is germanium. The form is made as one of the groups consisting of a shirt, pants, dress, underwear, clothing, and a sleeve.

Figure 11:
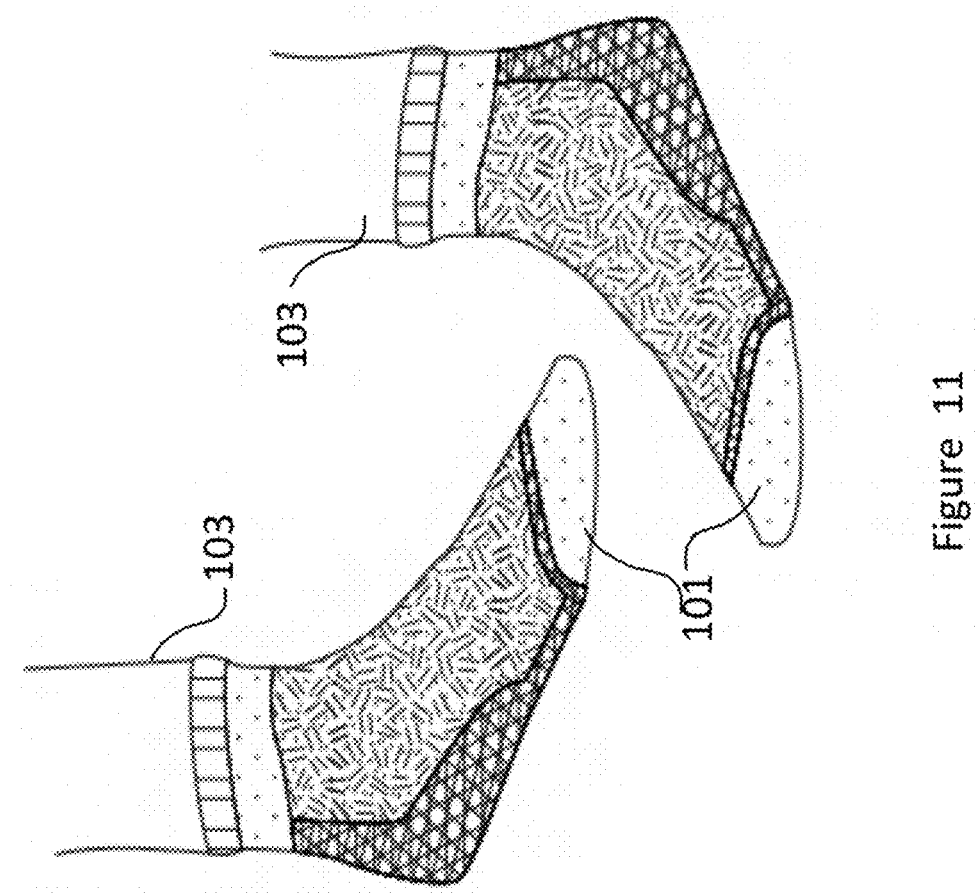
FIG. 11 shows a pair of ankle socks (one type of the apparel 101), in accordance with an exemplary embodiment of the invention.

FIG. 11 shows a pair of ankle socks (one type of the apparel 101), in accordance with an exemplary embodiment of the invention. When the pair of ankle socks are worn by the human then these pair of ankle socks touch the skin 103 and it creates gentle pressure on the feet and lower legs. This generates warmth which increases blood supply to the affected regions of the foot. This helps in subsiding the intensity of the pain and discomfort by flowing the more oxygenated blood into the feet.

Figure 12:
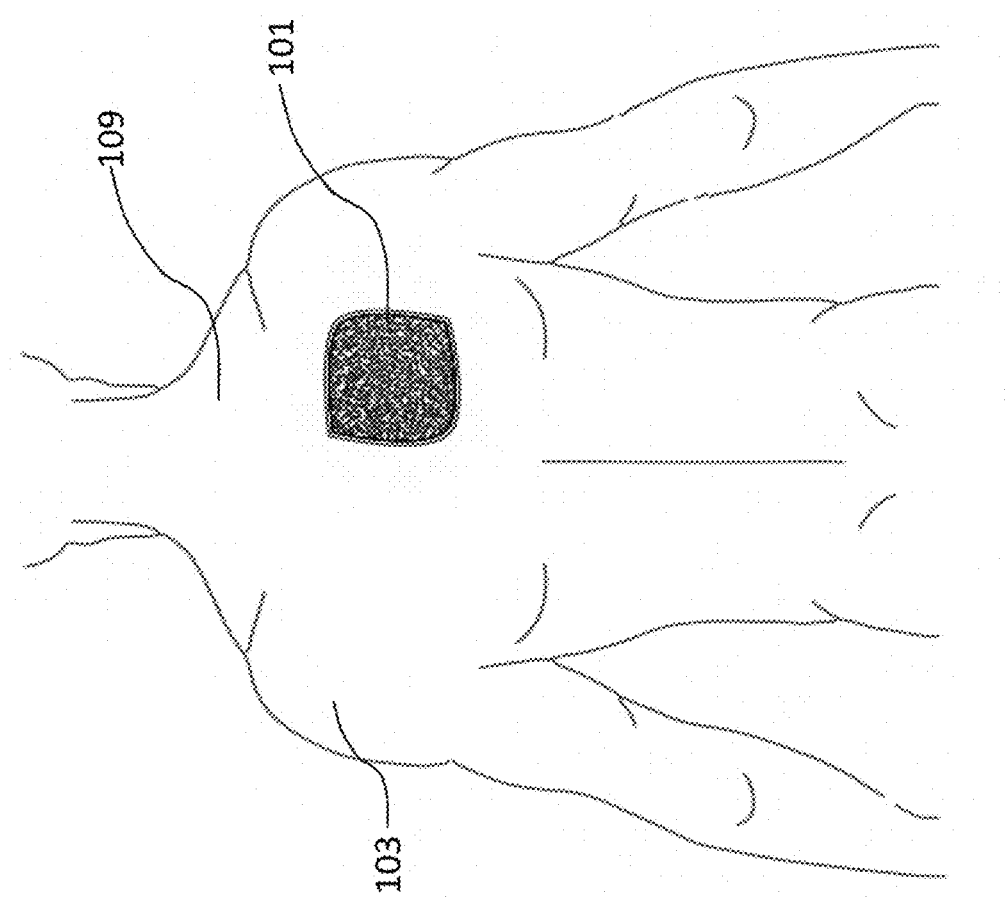
FIG. 12 shows a patch (one type of the apparel 101) that stick to any place of a human upper body part 109, in accordance with another exemplary embodiment of the invention.

FIG. 12 shows a patch (one type of the apparel 101) that stick to any place of a human upper body part 109, in accordance with another exemplary embodiment of the invention. When the patch is put on the skin 103 of the human upper body part 109 then it creates vibration around the area where this patch has been fixed and increases blood circulation of blood that area. This increased blood circulation helps in relieving pain and inflammation of the small area of the human upper body part 109.

Figure 13:
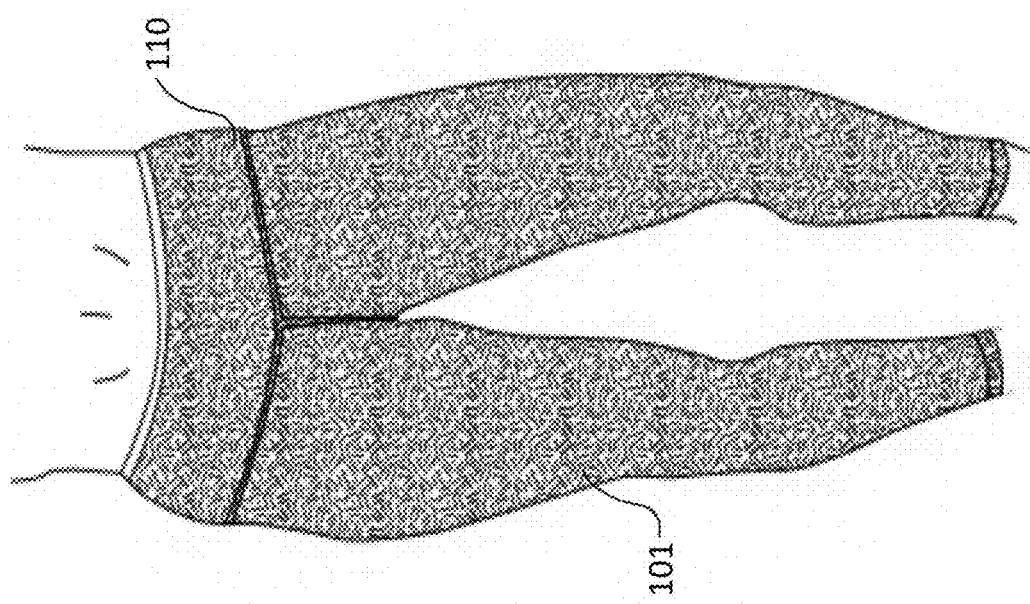
FIG. 13 shows a wearable full pant (one type of the apparel 101) in a human lower body part 110, in accordance with another exemplary embodiment of the invention.

FIG. 13 shows a wearable full pant (one type of the apparel 101) in a human lower body part 110, in accordance with another exemplary embodiment of the invention. When the human wears the full pant, then the fabric gets in contact with the human skin 103 and speeds up the blood circulation in that area in which the skin 103 and the fabric are in contact 102. This helps in reducing swelling and relieving the pain in that area where the skin 103 and the fabric are in contact 102.

Figure 14:
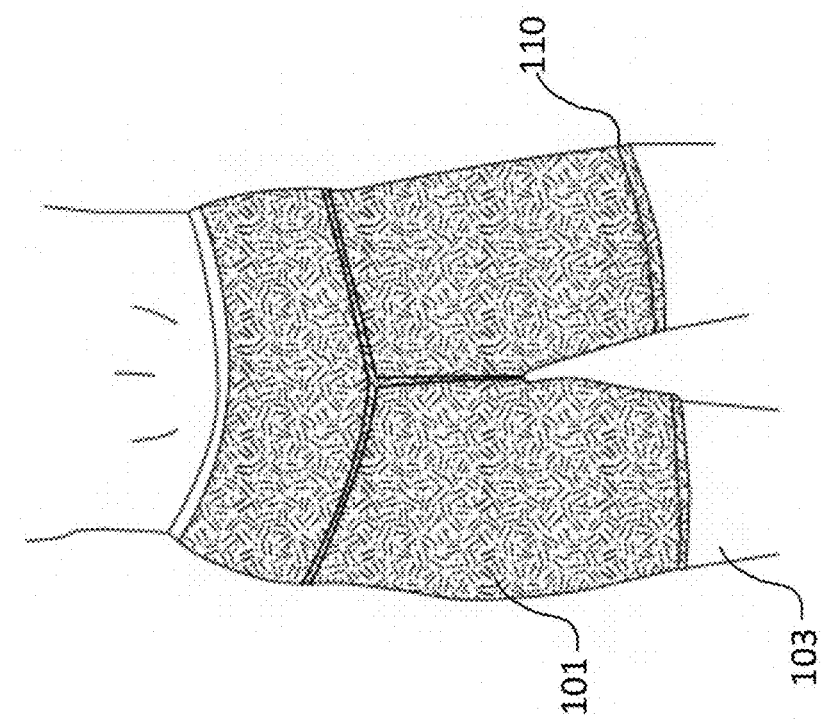
FIG. 14 shows a wearable half pant (one type of the apparel 101) in the human lower body part 110, in accordance with another exemplary embodiment of the invention.

FIG. 14 shows a wearable half pant (one type of the apparel 101) in the human lower body part 110, in accordance with another exemplary embodiment of the invention. When the human wears the half pant, then the fabric gets in contact with the human skin 103 and speeds up the blood circulation in that area in which the skin 103 and the fabric are in contact 102. This helps in reducing swelling and relieving the pain in that area where the skin 103 and the fabric are in contact 102.

Figure 15:
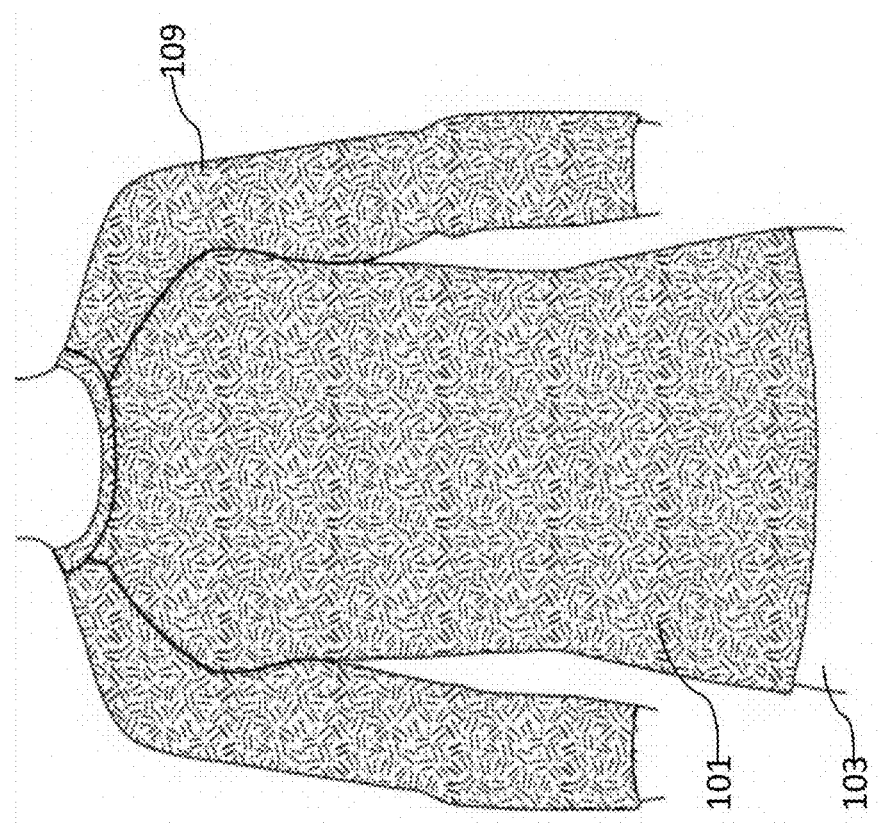
FIG. 15 shows a wearable full-sleeve top (one type of the apparel 101) in the human upper body part 109, in accordance with another exemplary embodiment of the invention.

FIG. 15 shows a wearable full-sleeve top (one type of the apparel 101) in the human upper body part 109, in accordance with another exemplary embodiment of the invention. When the human wears the full-sleeve top, then the fabric gets in contact with the human skin 103 and speeds up the blood circulation in that area in which the skin 103 and the fabric are in contact 102. This helps in reducing swelling and relieving the pain in that area by flowing the more oxygenated blood into the human upper body part 109.

Figure 16:
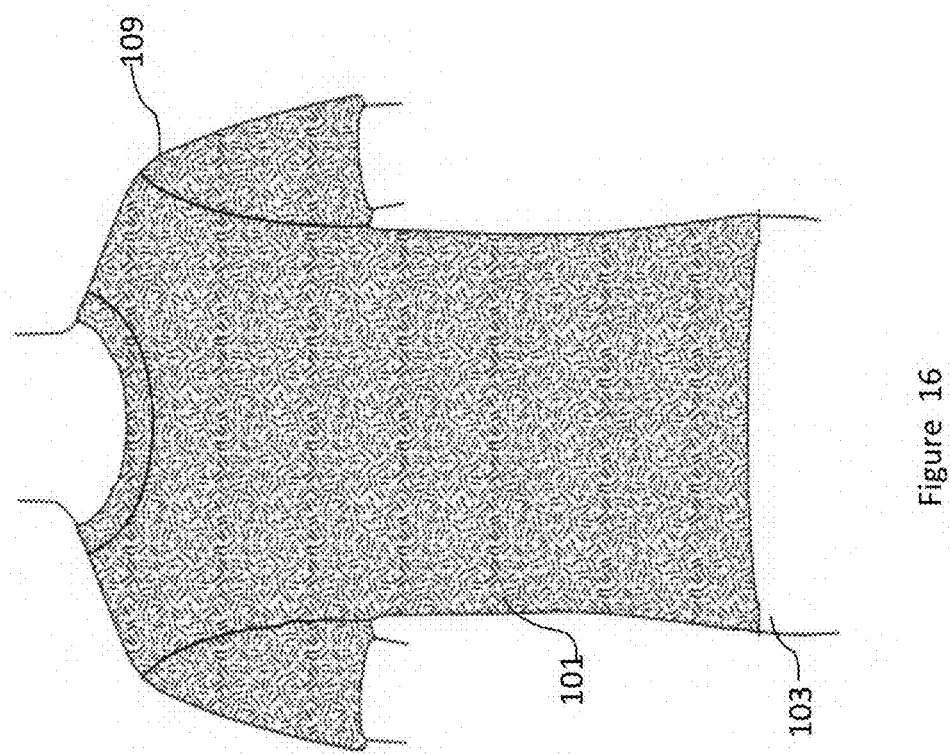
FIG. 16 shows a wearable half-sleeve top (one type of the apparel 101) in the human upper body part 109, in accordance with another exemplary embodiment of the invention.

FIG. 16 shows a wearable half-sleeve top (one type of the apparel 101) in the human upper body part 109, in accordance with another exemplary embodiment of the invention. When the human wears the half-sleeve top, then the fabric gets in contact with the human skin 103 and speeds up the blood circulation in that area in which the skin 103 and the fabric are in contact 102. This helps in reducing swelling and relieving the pain in that area by flowing the more oxygenated blood into the human upper body part 109.

Figure 17:
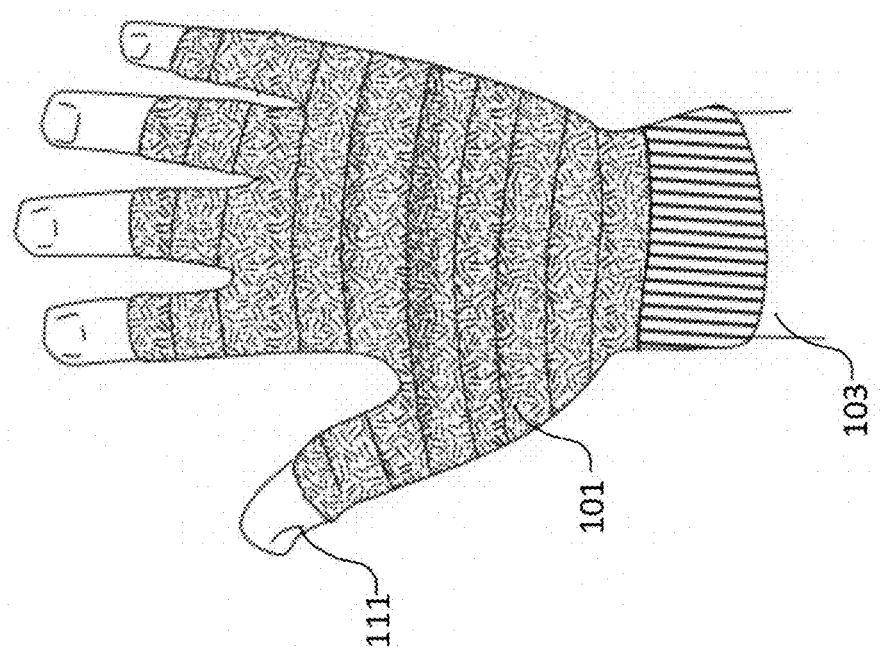
FIG. 17 shows a wearable finger-less gloves (one type of the apparel 101) in a human palm 111, in accordance with another exemplary embodiment of the invention.

FIG. 17 shows a wearable finger-less gloves (one type of the apparel 101) in a human palm 111, in accordance with another exemplary embodiment of the invention. When the human wears the finger-less gloves in the human palm 111, it creates pressure on the hands and increases blood flow inside the hand and also increases the temperature of the hand when the fabric of the finger-less gloves gets in contact 102 with the human skin 103. This helps in improving healing and eases pain and inflammation.

Figure 18:
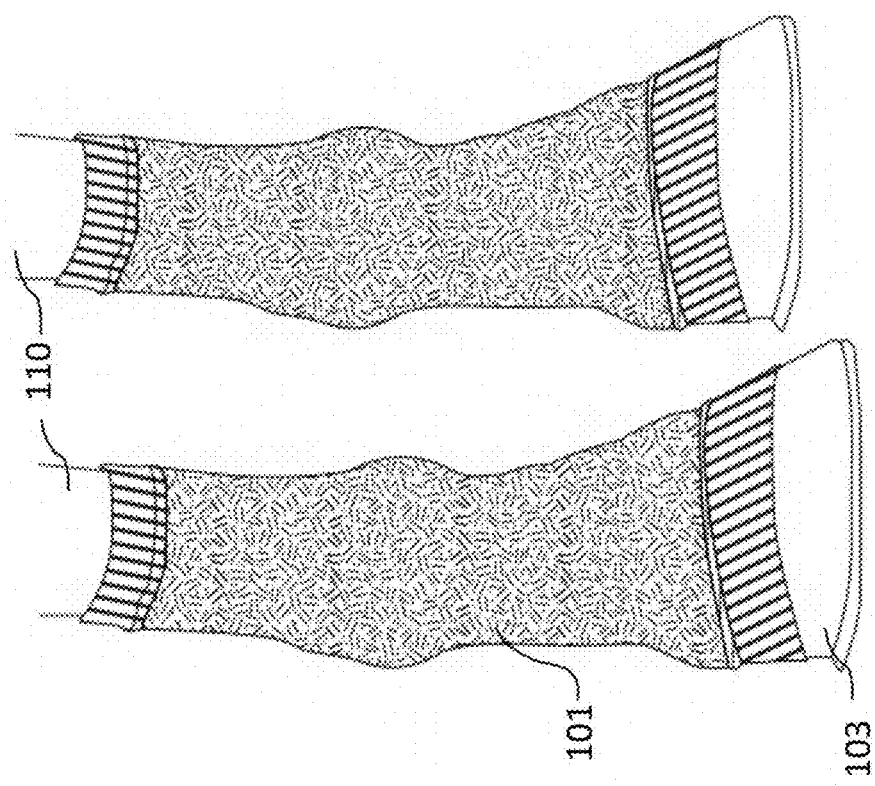
FIG. 18 shows a pair of hoof socks (one type of the apparel 101), in accordance with another exemplary embodiment of the invention.

FIG. 18 shows a pair of hoof socks (one type of the apparel 101), in accordance with another exemplary embodiment of the invention. When the pair of hoof socks are worn by the human then these pair of hoof socks touch the skin 103 and it increases the blood circulation inside the leg. The pair of hoof socks also incorporates semiconductor elements (like Germanium & Carbon) within its fabric, which when activated by body heat, release negative ions. The negative ions activate molecular vibrations that increase not only blood circulation but lymphatic flow as well. Increasing blood flow and speed and lymphatic drainage helps bring more oxygen and nutrients to the target area and clear out all the swelling and inflammation. Thus, it optimizes the body's natural healing process and accelerates recovery.

Part III—Manufacturing Process for Sleeves and Apparel Using the Invention

Figure 19:
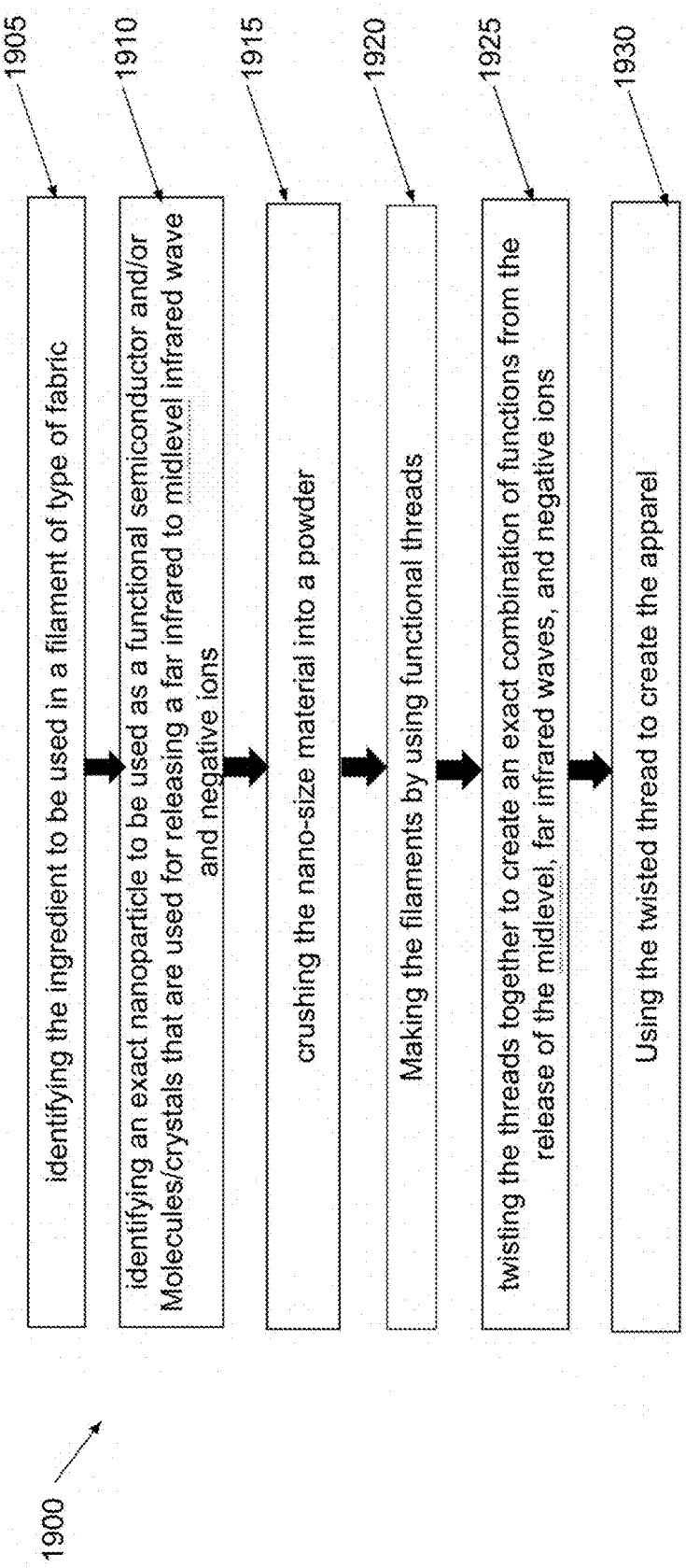
FIG. 19 is a flow chart illustrating a method 1900 for developing the apparel 101 by twisting multiple threads that positively affect the health and wellbeing of the mammal.

FIG. 19 is a flow chart illustrating a method 1900 for developing the apparel 101 by twisting multiple threads that positively affect the health and wellbeing of the mammal. The steps may be rearranged and may not follow the process in only the manner as depicted in the flow chart.

The method 1900 starts at step 1905 and proceeds to step 1910. At step 1905, identify the ingredient to be used in a filament of type of fabric. The ingredient is anyone of the cotton, the polyester, or the nylon.

At step 1910, identify an exact nanoparticle to be used as a functional semiconductor and/or Molecules/crystals that are used for releasing a far infrared to midlevel infrared wave and negative ions. The semiconductor is preferably the Germanium and the molecules or crystals is the Carbonized Charcoal which is preferably manufactured by the Bamboo charcoal.

At step 1915, the nano-size material is crushed into a powder and this is the technique that is used for grinding the coarse powder into fine particles up to 40 nanometers. Using a high-speed homogenizer, the nanoparticles are mixed with the filament type of fiber that is described in step 1905 and mixed with a high velocity for the filament entanglement. This process makes it difficult to wash out the powder.

At step 1920, the filaments are made by using functional threads. The filaments are anyone of the Germanium and the Carbonize charcoal.

At step 1925, twisting the threads together to create an exact combination of functions from the release of the midlevel, far infrared waves, and negative ions.

At step 1930, the twisted thread is then used to create the apparel 101 (e.g. an incrediwear product).

The method 1900 terminates at 1930, for example until invoked again. Alternatively, the method 1900 may repeat continuously or repeatedly or may execute as multiple instances of a multi-threaded process.

Figure 20:
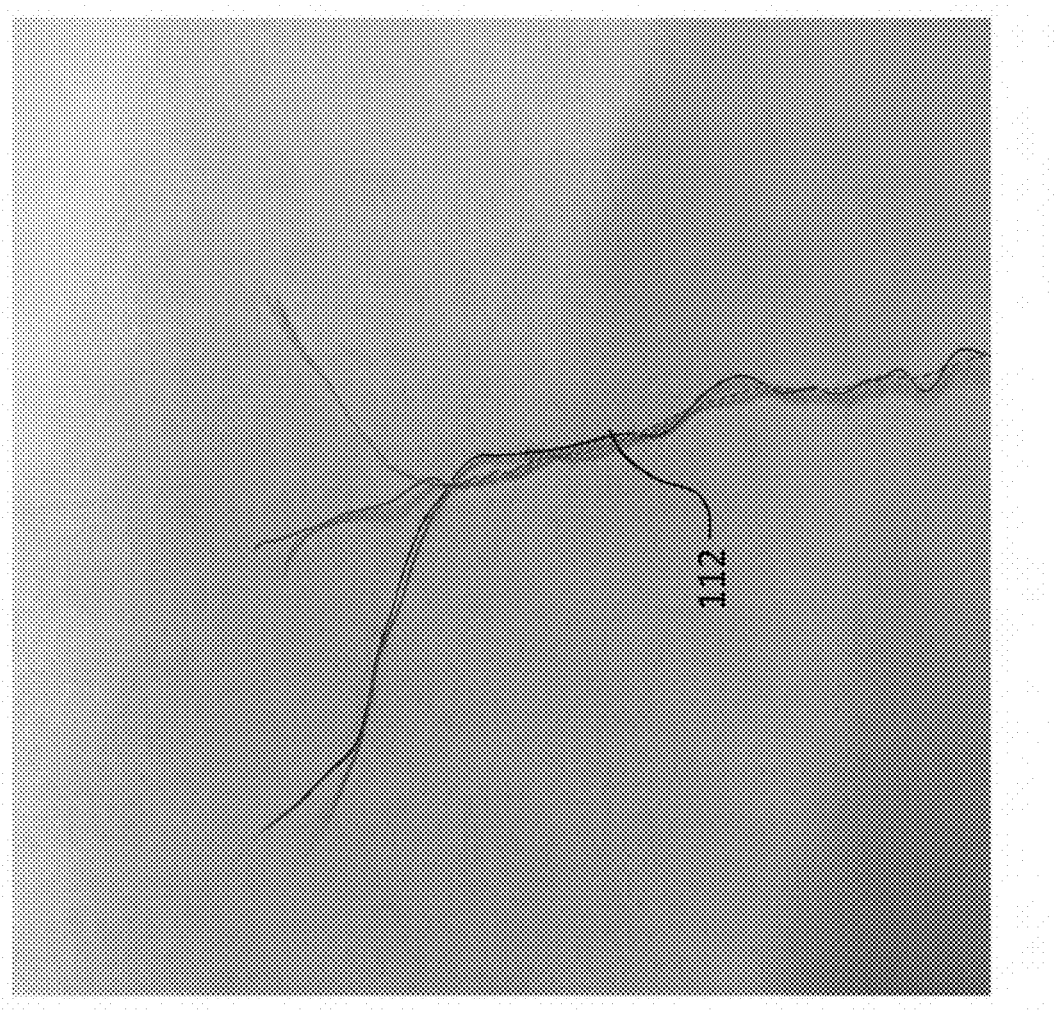
FIG. 20 shows a fiber thread 112, in accordance with another exemplary embodiment of the present invention.

FIG. 20 shows the fiber thread 112, in accordance with another exemplary embodiment of the present invention. The fiber thread 112 is anyone of the carbonized charcoal fiber thread or the germanium thread. The materials and apparel 101 may be prepared using the Carbonized charcoal fiber thread. The carbonized charcoal fiber is manufactured from the Taiwanese-grown bamboo (preferably 4 to 5 year old), is dried and burned at 800-1200 degrees C. in an oven until it is reduced to charcoal, it is then ground and filtered into nano-particles which are doped into the fibers of cotton, nylon or polyester, then spun into the yarn. The fiber yarn is then woven into knitted fabrics, and added to other fiber threads 112 to create double- or triple-fiber thread 112 yarn.

In accordance with another exemplary embodiment of the present invention, the materials and apparel 101 may be prepared using the Germanium thread. The germanium powder is grounded into nanoparticles. The Germanium Alloy fibers are made via high-temperature sintering (often over 1000 Celsius). Further, the nanoparticles are doped into the fibers of cotton, nylon, or polyester, similar to Carbonized charcoal fiber thread. The threads are then combined with other threads of fiber to create yarn. The material or apparel 101 is prepared by combining both thread types and weaving the threads into the finished products.

In accordance with an advantageous embodiment of the present invention, the Germanium alloy crystals (GAC) are piezoelectric materials and is a semiconductors. When a piezoelectric crystal is subjected to external forces, it automatically releases negative ions. The external forces may be a friction, heat, wave oscillations, light, etc., and may all stimulate negative ions. Its making is anti-static. The negative ions are like natural antioxidants because they may neutralize positive charges, such as H+, H2O2, etc., and prevent oxidation. The Germanium releases infrared waves when heated to 32 degrees. The nano-Germanium alloy is porous giving it a property to absorb odor. The Carbonized Charcoal is also porous giving it the property to absorb odor. The Carbonized Charcoal (CC) may release far infrared and is also a semiconductor that releases negative ions.

Part IV—Product Development Process for Making Material that is Customized to Deliver Health Benefits to Desired Areas of the Mammal's/Human's Body In accordance with an embodiment of the present invention, the creation of the material or apparel 101 is a step-by-step process and with each step, the created product is based on the body part which is being affected.

The material or apparel 101 may be created and specially formulated depending on the body part and function that is needed. The functions are included but not limited to reduced swelling, increased blood flux and speed, thermoregulation of temperature, reduced joint and muscle pain, improved ROM, reduced muscle fatigue, balance muscles, reduced headaches, reduced neuropathy pain, reduced fracture recovery time, reduced children's night growing pains, thermoregulate body while exercising, burn calories, change pH of the human cell, affect the ion transportation system of the cell membrane, and reduce cytokines.

In accordance with an exemplary embodiment of the present invention, firstly the apparel 101 is made for the back support with the combination of Germanium and Carbon. The body parts are the most important reason to determine the combination of Ge/Carbon. Further, the customization of the apparel 101 according to the body parts is based upon muscle density. The body parts are further divided into three sections, larger body parts, medium body parts, and thin body parts. The larger body parts include the knee, low back, and hip. The medium body parts include the shoulder and biceps. Further, the thin body parts include the calf, ankles, and wrists.

In accordance with an embodiment of the present invention, firstly the apparel 101 is made for the lower back support of the body. The lower back support is created without using neoprene and uses Germanium powder and bamboo charcoal threads to help with odor. Firstly, the researchers take a thread of Bamboo Charcoal embedded in a cotton/polyester blend and make a second thread using powder from germanium and mix it with PET (Polyethylene terephthalate) (the brace might not be washed, because it is not necessary that the Germanium would be washed out). Further, in the next process, the researchers used a twisted technique to combine the two threads together with a third thread of spandex to create one thread with at least three pieces (still have one of the original finished spools of thread).

Figure 21C:
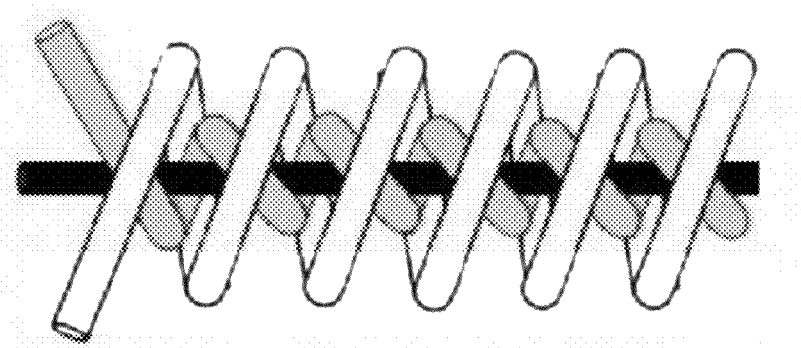
FIGS. 21(a)-(c) are a pictorial representation of three different structures of a composite yarn, in accordance with another exemplary embodiment of the present invention.
Figure 21B:
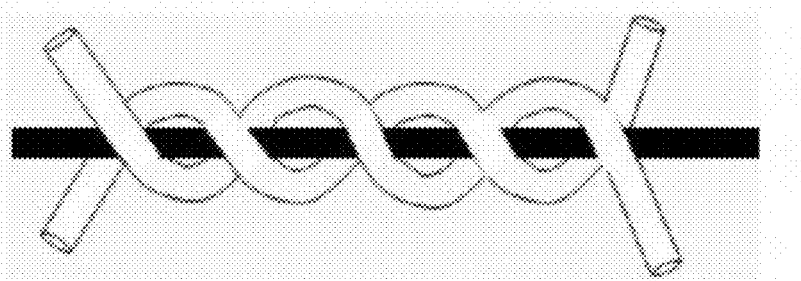
Figure 21A:
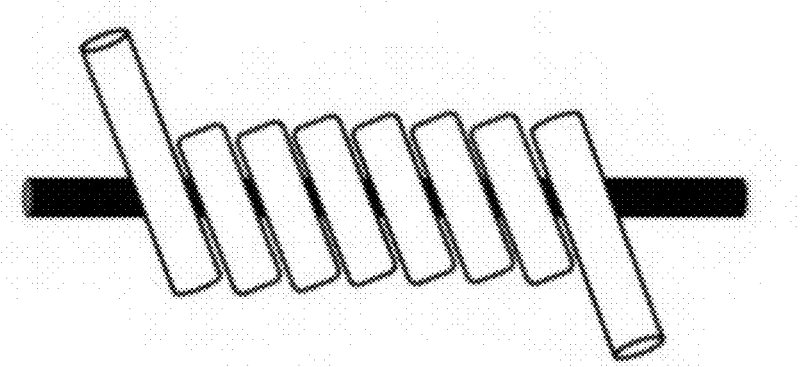

FIG. 21 is a pictorial representation of the three different structures of the composite yarn. This figure also shows the twisted thread techniques used to twist two or three different single threads. Generally, there is a core elastic thread, and the outside is nylon, cotton, or PET (from a polyester family). FIG. 21(a) shows a core spun yarn, FIG. 21(b) shows a co-mingled yarn, and FIG. 21(c) shows a covered yarn, in accordance with another exemplary embodiment of the present invention.

In accordance with another exemplary embodiment of the present invention, the process of making the thread is now refined. The thread is made with either BC/CC (Bamboo Charcoal/Carbonized Charcoal) or GE(Germanium). Depending on the body part, which is more muscular or more bony, the researcher choose the type of thread and the combination of BE and GE.

In accordance with another embodiment of the present invention, the GE (Germanium) is made by using polyester (PET) yarn. The PET yarn is compounded with the finely ground GE with making a master batch. Further, the batch is melted at 250° C., then polymerization occurs with regular PET and resin is created (as shown in FIG. 21).

In accordance with another exemplary embodiment of the present invention, the GE (Germanium) is made by using nylon yarn. The compound of nylon and powder of Ge is heated at 220-230 degree C. for 1 minute and then a resin is made.

In accordance with the above embodiment of the present invention, once the resin is made with either BC or GE, then the spool of thread is started. Further, the threads are then tested to identify the percentages of components GE or BC. Further, the threads are tested for wavelength and if the threads are in the active spectrum of far and mid-level infrared then a patch of material is created, and it is tested on the human.

In accordance with another embodiment of the present invention, the created threads are tested and are then twisted together to create one single thread with the at least three parts. The products are tested on the human body for checking the fitting of the apparel 101, the human feeling after wearing the apparel 101, and the functionality of the apparel 101. Once the fabric is tested by the wearers and it is determined that the apparel 101 is satisfactory then the plurality of sample sizes are created and tested. This process may take several weeks to months.

In accordance with another embodiment of the present invention, the single-thread development is used in the same manner as the twisted threads. Ge, and BC are mixed together into the powder and the same process is used as above to create a "Single Thread" instead of creating the need for the three separate threads combined into one. This process is done by three separate combinations of threads. The first one is PET with Ge/BC/jade, the second one is PET with Ge/BC, and the third one is Nylon with GE/BC/jade. These three compounds have never been combined into a single thread. The process is exactly the same as the above embodiment.

Part V—Formulations—Components and Concentration Ranges

FIG. 22 illustrates Table 2 which shows different components and concentrations ranges used for preparing apparel 101, in accordance with another exemplary embodiment of the invention.

In accordance with another embodiment of the present invention, the materials and apparel 101 include the at least one fiber that includes with the semiconductor in desired proportions, and are formed as knitted fabric with fibers. The fiber or fibers of the materials may include a thermoplastic material selected from the groups consisting of: Polyester, regular Polyethylene Terephalate, Cationic Dyeable Polyethylene Terephalate, High Tenacity Polyethylene, Fire Retardant Polyethylene Terephalate and Polyurethane, Polytrimethylene Terephthalate, Polybutylene Terephthalate, Nylon, Acrylic and Modacrylic. The material may include an artificial regenerated cellulosic material selected from the groups consisting of: Rayon, High Wet Modulus Rayon, Modal and Lyocell.

The fabric blends of the materials and apparel 101 may include Carbonized Charcoal, Cotton, Cotton (Germanium Infused), Cotton (Germanium/Carbonized Charcoal Infused), Germanium/Bamboo Charcoal Fiber, Polyester (Carbonized Charcoal Infused), Polyester, Polyester (Germanium/Carbonized Charcoal Infused), Polyester (Germanium Infused), Nylon (Germanium Infused) Nylon, Spandex, Rubber, Viscose, Wool fiber, Lycra. The materials may further include spandex, rubber, viscose or other elastic fibers to provide additional stretch ability and resilience.

The materials and apparel 101 may include carefully selected portions of the components which is being formed to reduce swelling, and pain or to provide fast healing of a wound. The compound composition and their concentration ranges for different products of different sizes are shown in the table 2.

In accordance with embodiment of the present invention, for upper-body human applications, the apparel 101 of the inventions may include a socks, a wrist sleeve, arm sleeve, shoulder brace, bandage wrap, back brace, circulation gloves and/or beanies. For lower-body human application, the apparel 101 of the inventions may include an ankle sleeve, calf sleeve, knee sleeve, leg sleeve, boot sleeve, hip brace. Asymmetrically-positioned material construction may also be applied in the apparel covering both a portion of the upper and lower body of a wearer (e.g., jumpsuits). The apparel 101 may be designed to be loose-fitting, "close-to-body" or snug-fitting, or even compression-fitting.

In accordance with another exemplary embodiment of the present invention, active low cut socks of size small (S), medium (M), large (L), extra-large (XL) are made by using 57% Bamboo Charcoal Fiber, 28% Cotton, and 15% Flexible Fiber. In another embodiment, the trek crew of size small (S), medium (M), large (L), extra-large (XL) are made by using 22% Bamboo Charcoal Fiber, 48% Cotton, 30% Flexible Fiber. In another embodiment, the knee brace size small (S), medium (M), large (L), extra-large (XL), XXL are made by using 49% Polyester(Carbon Infused), 25% Nylon (Germanium Infused), 21% Cotton(Germanium Infused), 5% Lycra Spandex.

In accordance with another advantageous embodiment of the present invention, the present invention provides comfort to a human by healing pain and swelling of their body. Further, the present invention is easy to adjust, light weight, breathable, comfortably support a skin-covered human body.

The inventions may also be described by the following numbered paragraphs:

1. A material for contacting a mammal with a skin-covered body that includes a region that is experiencing swelling, comprising:
    an expanse formed of a semiconductor and constructed for contact with the mammal; and
    wherein the expanse, upon contact with the region of the body, causes a decrease in the swelling.
2. The material as recited in paragraph 1, wherein the expanse is constructed for contact with the skin of the mammal.
3. The material as recited in paragraph 2, wherein the semiconductor is germanium.
4. The material as recited in paragraph 1, wherein the expanse, upon contact with the region of the body, eliminates the swelling.
5. The material as recited in paragraph 1, wherein the expanse is formed as a geometric shape.
6. The material as recited in paragraph 1, wherein the expanse is formed so that it has to be worn by the mammal.
7. The material as recited in paragraph 2, wherein the mammal is a human, and the expanse is formed so that has to be worn by the human.
8. Apparel for a human whose body includes a region that is experiencing swelling, comprising:
    a wearable form made of a semiconductor and constructed for contact with the human when the body is worn; and
    wherein the form, upon contact with the region of the human body, causes a decrease in the swelling.
9. The apparel as recited in paragraph 8, wherein the form is made for contact with the skin of the human body.
10. The apparel as recited in paragraph 9, wherein the semiconductor is germanium.
11. The apparel as recited in paragraph 8, wherein the form, upon contact with the region of the human body, eliminates the swelling.
12. The apparel as recited in paragraph 8, wherein the form is made as one of the group consisting of a shirt, pants, dress, underwear, clothing, and a sleeve.
13. Material for contacting a mammal with a skin-covered body that includes a region that has a wound that requires a first time to heal fully, comprising:
    an expanse formed of a semiconductor and constructed for contact with the mammal; and
    wherein the expanse, upon contact with the region of the body, causes the wound to heal in a second time that is less than the first time.
14. The material as recited in paragraph 13, wherein the expanse is constructed for contact with the skin of the mammal.
15. The material as recited in paragraph 14, wherein the semiconductor is germanium.
16. The material as recited in paragraph 13, wherein the expanse, upon contact with the region of the body, eliminates the swelling.
17. The material as recited in paragraph 13, wherein the expanse is formed as a geometric shape.
18. The material as recited in paragraph 13, wherein the expanse is formed so that it has to be worn by the mammal.
19. The material as recited in paragraph 14, wherein the mammal is a human, and the expanse is formed so that it has to be worn by the human.
20. Apparel for a human whose body includes a region that has a wound that requires a first time to heal fully, comprising:
    a wearable form made of a semiconductor and constructed for contact with the human when the body is worn; and
    wherein the form, upon contact with the region of the human body, causes the wound to heal in a second time that is less than the first time.
21. The apparel as recited in paragraph 20, wherein the form is made for contact with the skin of the human body.
22. The apparel as recited in paragraph 21, wherein the semiconductor is germanium.
23. The apparel as recited in paragraph 20, wherein the form, upon contact with the region of the human body, eliminates the swelling.
24. The apparel as recited in paragraph 20, wherein the form is made as one of the group consisting of a shirt, pants, dress, underwear, clothing, and a sleeve.

25. Material for contacting a mammal with a skin-covered body that includes a region that has a wound that requires a first time for the body to recover fully, comprising:
   an expanse formed of a semiconductor and constructed for contact with the mammal; and
   wherein the expanse, upon contact with the region of the body, causes the body to recover in a second time that is less than the first time.

26. The material as recited in paragraph 25, wherein the expanse is constructed for contact with the skin of the mammal.

27. The material as recited in paragraph 26, wherein the semiconductor is germanium.

28. The material as recited in paragraph 25, wherein the expanse, upon contact with the region of the body, eliminates the swelling.

29. The material as recited in paragraph 25, wherein the expanse is formed as a geometric shape.

30. The material as recited in paragraph 25, wherein the expanse is formed so that it has to be worn by the mammal.

31. The material as recited in paragraph 26, wherein the mammal is a human, and the expanse is formed so that it has to be worn by the human.

32 Apparel for a human whose body includes a region that has a wound that requires a first time for the body to recover fully, comprising:
   a wearable form made of a semiconductor and constructed for contact with the human when the body is worn; and
   wherein the form, upon contact with the region of the human body, causes the body to recover in a second time that is less than the first time.

33. The apparel as recited in paragraph 32, wherein the form is made for contact with the skin of the human body.

34. The apparel as recited in paragraph 33, wherein the semiconductor is germanium.

35. The apparel as recited in paragraph 32, wherein the form, upon contact with the region of the human body, eliminates the swelling.

36. The apparel as recited in paragraph 32, wherein the form is made as one of the group consisting of a shirt, pants, dress, underwear, clothing, and a sleeve.

37. Material for contacting a mammal with a skin-covered body that includes mobile cells that move within the body and exhibit cellular movement at a first rate, comprising:
   an expanse formed of a semiconductor and constructed for contact with the mammal; and
   wherein the expanse, upon contact with the region of the body, causes the cellular movement to occur at a second rate that is greater than the first rate.

38. The material as recited in paragraph 37, wherein the expanse is constructed for contact with the skin of the mammal.

39. The material as recited in paragraph 38, wherein the semiconductor is germanium.

40. The material as recited in paragraph 37, wherein the expanse, upon contact with the region of the body, eliminates the swelling.

41. The material as recited in paragraph 37, wherein the expanse is formed as a geometric shape.

42. The material as recited in paragraph 37, wherein the expanse is formed so that it has to be worn by the mammal.

43. The material as recited in paragraph 38, wherein the mammal is a human, and the expanse is formed so that it has to be worn by the human.

44. Apparel for the human whose body includes mobile cells that move within the body and exhibit cellular movement at a first rate, comprising:
   a wearable form made of a semiconductor and constructed for contact with the human when the body is worn; and
   wherein the form, upon contact with the region of the human body, causes the cellular movement to occur at a second rate that is greater than the first rate.

45. The apparel as recited in paragraph 44, wherein the form is made for contact with the skin of the human body.

46. The apparel as recited in paragraph 45, wherein the semiconductor is germanium.

47. The apparel as recited in paragraph 44, wherein the form, upon contact with the region of the human body, eliminates the swelling.

48. The apparel as recited in paragraph 44, wherein the form is made as one of the group consisting of a shirt, pants, dress, underwear, clothing, and a sleeve.

49. Material for contacting a mammal with a skin-covered body that is capable of receiving external optical waves, comprising:
   an expanse formed of a semiconductor and constructed for contact with the mammal; and
   wherein the expanse, upon contact with the region of the body, causes an external mid-IR optical wave to be received by the body.

50. The material as recited in paragraph 49, wherein the expanse is constructed for contact with the skin of the mammal.

51. The material as recited in paragraph 50, wherein the semiconductor is germanium.

52. The material as recited in paragraph 49, wherein the expanse, upon contact with the region of the body, eliminates the swelling.

53. The material as recited in paragraph 49, wherein the expanse is formed as a geometric shape.

54. The material as recited in paragraph 49, wherein the expanse is formed so that it has to be worn by the mammal.

55. The material as recited in paragraph 50, wherein the mammal is a human, and the expanse is formed so that it has to be worn by the human.

56. Apparel for a human whose body is capable of receiving an optical wave, comprising:
   a wearable form made of a semiconductor and constructed for contact with the human when the body is worn; and
   wherein the form, upon contact with the region of the human body, causes an external mid-IR optical wave to be received by the body.

57. The apparel as recited in paragraph 56, wherein the form is made for contact with the skin of the human body.

58. The apparel as recited in paragraph 57, wherein the semiconductor is germanium.

59. The apparel as recited in paragraph 56, wherein the form, upon contact with the region of the human body, eliminates the swelling.

60. The apparel as recited in paragraph 56, wherein the form is made as one of the group consisting of a shirt, pants, dress, underwear, clothing, and a sleeve.

61. Material for contacting a mammal with a skin-covered body that is capable of experiencing temperature changes in spite of being warm-blooded, comprising:
   an expanse formed of a semiconductor and constructed for contact with the mammal; and
   wherein the expanse, upon contact with the region of the body, promotes thermoregulation of the body.

62. The material as recited in paragraph 61, wherein the expanse, upon contact with the region of the body, promotes thermoregulation by cooling the body when it exceeds a first temperature, and heating it when it falls below a second temperature.

63. The material as recited in paragraph 62, wherein the expanse is constructed for contact with the skin of the mammal.

64. The material as recited in paragraph 63, wherein the semiconductor is germanium.

65. The material as recited in paragraph 64, wherein the expanse, upon contact with the region of the body, causes thermoregulation of the body.

66. The material as recited in paragraph 65, wherein the expanse is formed as a geometric shape.

67. The material as recited in paragraph 66, wherein the expanse is formed so that it has to be worn by the mammal.

68. The material as recited in paragraph 64, wherein the mammal is a human, and the expanse is formed so that it has to be worn by the human.

69. Apparel for a human whose skin-covered, tissue-containing body is capable of experiencing temperature changes in spite of being warm-blooded, comprising:
a wearable form made of a semiconductor and constructed for contact with the human when the body is worn; and
wherein the form, upon contact with the region of the human body, promotes thermoregulation of the body.

70. The apparel as recited in paragraph 69, wherein the form, upon contact with the region of the body, promotes thermoregulation by cooling the body when it exceeds a first temperature, and heating it when it falls below a second temperature.

71. The apparel as recited in paragraph 70, wherein the form is made for contact with the skin of the human body.

72. The apparel as recited in paragraph 71, wherein the semiconductor is germanium.

73. The apparel as recited in paragraph 70, wherein the form, upon contact with the skin, causes thermoregulation.

74. The apparel as recited in paragraph 73, wherein the form is made as one of the group consisting of a shirt, pants, dress, underwear, clothing, and a sleeve.

75. Material for contacting a mammal with a skin-covered body that has arthritis, experiences pain, and has decreased physical capabilities due to the arthritis, comprising:
an expanse formed of a semiconductor and constructed for contact with the mammal; and
wherein the expanse, upon contact with the region of the body, treats the arthritis by reducing pain and improving physical capabilities chosen from the groups consisting of grip and range of motion.

76. The material as recited in paragraph 75, wherein the expanse is constructed for contact with the skin of the mammal.

77. The material as recited in paragraph 75, wherein the semiconductor is germanium.

78. The material as recited in paragraph 75, wherein the expanse is formed as a geometric shape.

79. The material as recited in paragraph 75, wherein the expanse is formed so that it has to be worn by the mammal.

80. The material of paragraph 77, wherein the mammal is a human, and the expanse is formed so that it has to be worn by the human.

81. Apparel for a human whose skin-covered body has arthritis, experiences pain, and has decreased physical capabilities due to the arthritis, comprising:
a wearable form made of a semiconductor and constructed for contact with the human when the body is worn; and
wherein the form, upon contact with the region of the human body, treats the arthritis by reducing pain and improving physical capabilities chosen from the groups consisting of grip and range of motion.

82. The apparel as recited in paragraph 81, wherein the form is made for contact with the skin of the human body.

83. The apparel as recited in paragraph 81, wherein the semiconductor is germanium.

84. The apparel as recited in paragraph 82, wherein the form is made as one of the group consisting of a shirt, pants, dress, underwear, clothing, and a sleeve.

85. Material for contacting a mammal with a skin-covered body that is further capable of playing sports and getting sports injuries, comprising:
an expanse formed of a semiconductor and constructed for contact with the mammal; and
wherein the expanse, upon contact with the region of the body, tends to prevent sports injuries.

86. The material as recited in paragraph 85, wherein the expanse is constructed for contact with the skin.

87. The material as recited in paragraph 86, wherein the semiconductor is germanium.

88. The material as recited in paragraph 85, wherein the expanse, upon contact with the region of the body, prevents sports injuries.

89. The material as recited in paragraph 87, wherein the expanse is formed as a geometric shape.

90. The material as recited in paragraph 88, wherein the expanse is formed so that it has to be worn by the human.

91. Apparel for a human with a skin-covered body that is capable of playing sports and getting sports injuries, comprising:
a wearable form made of a semiconductor and constructed for contact with the human when the body is worn; and
wherein the form, upon contact with the region of the human body, tends to prevent sports injuries.

92. The apparel as recited in paragraph 91, wherein the form is made for contact with the skin.

93. The apparel as recited in paragraph 91, wherein the semiconductor is germanium.

94. The apparel as recited in paragraph 91, wherein the form, upon contact with the region of the human body, prevents sports injuries.

95. The apparel as recited in paragraph 91, wherein the form is made as one of the group consisting of a shirt, pants, dress, underwear, clothing, and a sleeve.

96. Material for contacting a mammal with a skin-covered body that has a neurological system, tissue, and blood that includes nutrient-containing hemoglobin, and the tissue is capable of being oxygenated and receiving nutrients by the hemoglobin in the blood that flows through the tissue, comprising:
an expanse formed of a semiconductor and constructed for contact with the mammal; and
wherein the expanse, upon contact with the region of the body, tends to decrease neuropathy in the body.

97. The material as recited in paragraph 96, wherein the expanse, upon contact with the region of the body, tends to decrease neuropathy by increasing the flow of hemoglobin-containing blood through the tissue.

98. The material as recited in paragraph 96, wherein the expanse is constructed for contact with the skin.

99. The material as recited in paragraph 96, wherein the semiconductor is germanium.

100. The material as recited in paragraph 96, wherein the expanse is formed as a geometric shape.

101. The material as recited in paragraph 96, wherein the expanse is formed so that it has to be worn by the human.

102. Apparel for a human with a skin-covered body that has a neurological system, tissue, and blood that includes nutrient-containing hemoglobin, and the tissue is capable of being oxygenated and receiving nutrients by the hemoglobin in the blood that flows through the tissue, comprising:
a wearable form made of a semiconductor and constructed for contact with the human when the body is worn; and
wherein the form, upon contact with the region of the human body, tends to decrease neuropathy in the body.

103. The apparel as recited in paragraph 102, wherein the expanse, upon contact with the region of the body, tends to decrease neuropathy by increasing the flow of hemoglobin-containing blood through the tissue.

104. The apparel as recited in paragraph 102, wherein the form is made for contact with the skin.

105. The apparel as recited in paragraph 102, wherein the semiconductor is germanium.

106. The apparel as recited in paragraph 102, wherein the form is made as one of the group consisting of a shirt, pants, dress, underwear, clothing, and a sleeve.

107. Material for contacting a mammal with a skin-covered body that has cognitive function and is capable of experiencing a concussion that causes headaches, comprising:
an expanse formed of a semiconductor and constructed for contact with the mammal; and
wherein the expanse, upon contact with the region of the body, tends to promote healing after a concussion.

108. The material as recited in paragraph 107, wherein the expanse, upon contact with the region of the body, tends to promote healing after the concussion by restoring cognitive function and, as a result, tends to reduce headaches.

109. The material as recited in paragraph 107, wherein the expanse is constructed for contact with the skin.

110. The material as recited in paragraph 107, wherein the semiconductor is germanium.

111. The material as recited in paragraph 107, wherein the expanse is formed as a geometric shape.

112. The material as recited in paragraph 107, wherein the expanse is formed so that it has to be worn by the human.

113. Apparel for a human with a skin-covered body that has cognitive function and is capable of experiencing a concussion that causes headaches, comprising:
a wearable form made of a semiconductor and constructed for contact with the human when the body is worn; and
wherein the form, upon contact with the region of the human body, tends to promote healing after a concussion.

114. The apparel as recited in paragraph 113, wherein the expanse, upon contact with the region of the body, tends to promote healing after the concussion by restoring cognitive function and, as a result, tends to reduce headaches.

115. The apparel as recited in paragraph 113, wherein the form is made for contact with the skin.

116. The apparel as recited in paragraph 113, wherein the semiconductor is germanium.

117. The apparel as recited in paragraph 113, wherein the form is made as one of the group consisting of a shirt, pants, dress, underwear, clothing, and a sleeve.

118. Material for contacting a mammal with a skin-covered body that is capable of experiencing headaches, comprising:
an expanse formed of a semiconductor and constructed for contact with the mammal; and
wherein the expanse, upon contact with the region of the body, tends to reduce headaches.

119. The material as recited in paragraph 118, wherein the expanse, upon contact with the region of the body, tends to eliminate headaches.

120. The material as recited in paragraph 118, wherein the expanse is constructed for contact with the skin.

121. The material as recited in paragraph 118, wherein the semiconductor is germanium.

122. The material as recited in paragraph 118, wherein the expanse is formed as a geometric shape.

123. The material as recited in paragraph 118, wherein the expanse is formed so that it has to be worn by the human.

124. Apparel for a human with a skin-covered body that is capable of experiencing headaches, comprising:
a wearable form made of a semiconductor and constructed for contact with the human when the body is worn; and
wherein the form, upon contact with the region of the human body, tends to tends to reduce headaches.

125. The apparel as recited in paragraph 124, wherein the expanse, upon contact with the region of the body, tends to eliminate headaches.

126. The apparel as recited in paragraph 124, wherein the form is made for contact with the skin.

127. The apparel as recited in paragraph 124, wherein the semiconductor is germanium.

128. The apparel as recited in paragraph 124, wherein the form is made as one of the group consisting of a shirt, pants, dress, underwear, clothing, and a sleeve.

129. A material for contacting the mammal with the skin-covered body that contains positive ions, comprising:
an expanse formed of a semiconductor and constructed for contact with the mammal; and
wherein the expanse, upon contact with the region of the body, releases negative ions that enter the body and pair with the positive ions, causing an exothermic reaction that cools the body adjacent the region where the pairing of negative ions and positive ions occurs; and 130. The material as recited in paragraph 129, wherein the expanse is constructed for contact with the skin.

131. The material as recited in paragraph 129, wherein the semiconductor is germanium.

132. The material as recited in paragraph 129, wherein the expanse is formed as a geometric shape.

133. The material as recited in paragraph 129, wherein the expanse is formed so that it has to be worn by the human.

134. Apparel for a human with a skin-covered body that contains positive ions, comprising:
a wearable form made of a semiconductor and constructed for contact with the human when the body is worn; and
wherein the form, upon contact with the region of the human body, releases negative ions that enter the body and pair with the positive ions, causing an exothermic reaction that cools the body adjacent the region where the pairing of negative ions and positive ions occurs.

135. The apparel as recited in paragraph 134, wherein the form is made for contact with the skin.

136. The apparel as recited in paragraph 134, wherein the semiconductor is germanium.

137. The apparel as recited in paragraph 134, wherein the form is made as one of the group consisting of a shirt, pants, dress, underwear, clothing, and a sleeve.

138. Material for contacting a mammal with a skin-covered body that is capable of experiencing muscle load, comprising:
an expanse formed of a semiconductor and constructed for contact with the mammal; and
wherein the expanse, upon contact with the region of the body, tends to decrease muscle load in the body.

139. The material as recited in paragraph 138, wherein the expanse is constructed for contact with the skin.

140. The material as recited in paragraph 138, wherein the semiconductor is germanium.

141. The material as recited in paragraph 138, wherein the expanse is formed as a geometric shape.

142. The material as recited in paragraph 138, wherein the expanse is formed so that it has to be worn by the human.

143. Apparel for a human with a skin-covered body that is capable of experiencing muscle load, comprising:
a wearable form made of a semiconductor and constructed for contact with the human when the body is worn; and
wherein the form, upon contact with the region of the human body, tends to decrease muscle load in the body.

144. The apparel a recited in paragraph 143, wherein the form is made for contact with the skin.

145. The apparel a recited in paragraph 143, wherein the semiconductor is germanium.

146. The apparel a recited in paragraph 143, wherein the form is made as one of the group consisting of a shirt, pants, dress, underwear, clothing, and a sleeve.

147. Material for contacting a mammal with a skin-covered body that includes tissue, blood vessels and cells, and in which there is interstitial fluid pressure that relates to interstitial fluid that is extracellular and outside of blood vessels, comprising:
an expanse formed of a semiconductor and constructed for contact with the mammal; and
wherein the expanse, upon contact with the region of the body, tends to increase the interstitial fluid pressure in the body.

148. The material as recited in paragraph 147, wherein the expanse is constructed for contact with the skin.

149. The material as recited in paragraph 147, wherein the semiconductor is germanium.

150. The material as recited in paragraph 147, wherein the expanse is formed as a geometric shape.

151. The material as recited in paragraph 147, wherein the expanse is formed so that it has to be worn by the human.

152. Apparel for a human with a skin-covered body that includes tissue, blood vessels and cells, and in which there is interstitial fluid pressure that relates to interstitial fluid that is extracellular and outside of blood vessels, comprising:
a wearable form made of a semiconductor and constructed for contact with the human when the body is worn; and
wherein the form, upon contact with the region of the human body, tends to increase the interstitial fluid pressure in the body.

153. The apparel as recited in paragraph 152, wherein the form is made for contact with the skin.

154. The apparel as recited in paragraph 152, wherein the semiconductor is germanium.

155. The apparel as recited in paragraph 152, wherein the form is made as one of the group consisting of a shirt, pants, dress, underwear, clothing, and a sleeve.

156. Material for contacting a mammal with a skin-covered body that includes a brain, sensory receptors, muscles, and a proprioception system, comprising:
an expanse formed of a semiconductor and constructed for contact with the mammal; and
wherein the expanse, upon contact with the region of the body, tends to balance the muscles in the body by creating a proprioceptive response within the proprioception system.

157. The material as recited in paragraph 156, wherein the expanse is constructed for contact with the skin.

158. The material as recited in paragraph 156, wherein the semiconductor is germanium.

159. The material as recited in paragraph 156, wherein the expanse is formed as a geometric shape.

160. The material as recited in paragraph 156, wherein the expanse is formed so that it has to be worn by the human.

161. Apparel for a human with a skin-covered body that includes a brain, sensory receptors, muscles, and a proprioception system, comprising:
a wearable form made of a semiconductor and constructed for contact with the human when the body is worn; and
wherein the form, upon contact with the region of the human body, tends to balance the muscles in the body by creating a proprioceptive response within the proprioception system.

162. The apparel as recited in paragraph 161, wherein the form is made for contact with the skin.

163. The apparel as recited in paragraph 161, wherein the semiconductor is germanium.

164. The apparel as recited in paragraph 161, wherein the form is made as one of the group consisting of a shirt, pants, dress, underwear, clothing, and a sleeve.

Embodiments are described at least in part herein with reference to flowchart illustrations and/or block diagrams of methods and systems, according to embodiments of the disclosure. Where appropriate and practical, a block of the illustrations, and combinations of blocks, can be implemented by computer program instructions. These computer program instructions may be provided to a processor of a general-purpose computer, special purpose computer, or other programmable data processing apparatus to produce a machine such that the instructions, which execute via the processor of the computer or other programmable data processing apparatus, create means for implementing the functions/acts specified in the block or blocks.

What is claimed:

1. A material for contacting a mammal having a skin-covered body with a region having soft tissue with inflammation comprising:
an expanse constructed for contact with the region of the body;
the expanse comprising a plurality of woven threads, each thread comprising a combination of at least three components including:
a first material comprising a plurality of fibers;
a plurality of semiconductor nanoparticles compounded with the fibers configured to release external mid-IR optical waves in the region of the body responsive to body heat;
a plurality of charcoal nanoparticles compounded with the fibers configured to release infrared waves in the region of the body responsive to the body heat;
the semiconductor nanoparticles configured to reduce the inflammation upon the contact with the region of the body using a transdermal effect from the mid-IR optical waves penetrating the soft tissue in the region responsive to the body heat.

2. The material of claim 1 wherein the first material comprises cotton, nylon or polyester, the semiconductor nanoparticles comprise germanium, and the charcoal nanoparticles comprise bamboo charcoal or carbonized charcoal.

3. The material of claim 1 wherein the region of the body comprises a body part and a percentage of the semiconductor nanoparticles and the charcoal nanoparticles in the first material is selected according to the body part.

4. The material of claim 1 wherein the first material comprises polyester, the charcoal nanoparticles comprise bamboo charcoal and the semiconductor nanoparticles comprise germanium.

5. The material of claim 1 wherein the first material comprises nylon, the charcoal nanoparticles comprise bamboo charcoal and the semiconductor nanoparticles comprise germanium.

6. The material of claim 1 wherein each thread also includes jade combined with the first material.

7. The material as claimed in of claim 1 wherein the mid-IR optical waves have wavelengths in a mid-infrared (mid-IR) spectral region, which spans 3-30 µm.

8. An apparel for a human having a body with a region having soft tissue with inflammation comprising:
- a wearable form constructed for contact with the region of the body;
- the form comprising a plurality of woven threads, each thread comprising a combination of at least three components including:
  - a first material comprising a plurality of fibers;
  - a plurality of semiconductor nanoparticles compounded with the fibers configured to release external mid-IR optical waves in the region of the body responsive to body heat;
  - a plurality of charcoal nanoparticles compounded with the fibers configured to release infrared waves in the region of the body responsive to the body heat;
  - the semiconductor nanoparticles configured to reduce the inflammation upon the contact with the region of the body using a transdermal effect from the mid-IR optical waves penetrating the soft tissue in the region responsive to the body heat.

9. The apparel of claim 8 wherein the first material comprises cotton, nylon or polyester, the semiconductor nanoparticles comprise germanium, and the charcoal nanoparticles comprise bamboo charcoal or carbonized charcoal.

10. The apparel of claim 8 wherein the region of the body comprises a body part and a percentage of the semiconductor nanoparticles and the charcoal nanoparticles in the first material is selected according to the body part.

11. The apparel of claim 8 wherein each thread also includes jade combined with the first material.

12. The apparel of claim 8 wherein the mid-IR optical waves have wavelengths in a mid-infrared (mid-IR) spectral region, which spans 3-30 µm.

* * * * *